United States Patent
Kawamoto et al.

(10) Patent No.: US 10,731,133 B2
(45) Date of Patent: Aug. 4, 2020

(54) METHOD FOR PRODUCING RENAL PROGENITOR CELLS

(71) Applicants: Astellas Pharma Inc., Chuo-ku, Tokyo (JP); KYOTO UNIVERSITY, Kyoto-shi, Kyoto (JP)

(72) Inventors: Tatsuya Kawamoto, Tokyo (JP); Yukiko Yamagishi, Tokyo (JP); Kenji Osafune, Kyoto (JP)

(73) Assignees: Astellas Pharma Inc., Tokyo (JP); Kyoto University, Kyoto (JP)

( * ) Notice: Subject to any disclaimer, the term of this patent is extended or adjusted under 35 U.S.C. 154(b) by 16 days.

(21) Appl. No.: 15/758,580

(22) PCT Filed: Sep. 9, 2016

(86) PCT No.: PCT/JP2016/077353
§ 371 (c)(1),
(2) Date: Mar. 8, 2018

(87) PCT Pub. No.: WO2017/043666
PCT Pub. Date: Mar. 16, 2017

(65) Prior Publication Data
US 2018/0273905 A1    Sep. 27, 2018

(30) Foreign Application Priority Data
Sep. 11, 2015 (JP) .................. 2015-179104

(51) Int. Cl.
| | |
|---|---|
| A01N 61/00 | (2006.01) |
| C12N 5/02 | (2006.01) |
| C12N 5/071 | (2010.01) |
| G01N 33/53 | (2006.01) |
| C12N 5/10 | (2006.01) |
| C12Q 1/04 | (2006.01) |
| A61K 35/22 | (2015.01) |
| C12N 15/09 | (2006.01) |

(52) U.S. Cl.
CPC ............ *C12N 5/0687* (2013.01); *A61K 35/22* (2013.01); *C12N 5/10* (2013.01); *C12Q 1/04* (2013.01); *A01N 61/00* (2013.01); *C12N 15/09* (2013.01); *C12N 2506/02* (2013.01); *C12N 2506/45* (2013.01); *G01N 33/53* (2013.01)

(58) Field of Classification Search
CPC ............ C12N 5/0687; C12N 2506/02; C12N 2506/45; A01N 61/00; G01N 33/53
USPC .............................. 435/377, 369, 7.1; 514/1
See application file for complete search history.

(56) References Cited

U.S. PATENT DOCUMENTS
5,843,780 A    12/1998  Thomson
2015/0071886 A1    3/2015  Houze et al.

FOREIGN PATENT DOCUMENTS

| | | |
|---|---|---|
| EP | 1970446 A1 | 9/2008 |
| EP | 3020803 A1 | 5/2016 |
| JP | 2014-520523 A | 8/2014 |
| WO | WO 2007/069666 A1 | 6/2007 |
| WO | WO 2010/047824 A1 | 4/2010 |
| WO | WO 2010/097793 A2 | 9/2010 |
| WO | WO 2012/011610 A1 | 1/2012 |
| WO | WO 2014/200115 A1 | 12/2014 |
| WO | WO-2015/014731 A1 | 2/2015 |

OTHER PUBLICATIONS

Romagnani et al., 2016, US 20160333318 A1, effective filing date, Dec. 24, 2013.*
Kim et al., 2014, IOVS, vol. 55, No. 8, pp. 5099-5108.*
Stern-Straeter et al., 2014, International Journal of Molecular Medicine, vol. 33, pp. 160-170.*
Romito et al., 2016, Hindawi Publishing Corporation, Stem Cell International, vol. 2016, Article ID 9451492, pp. 1-20.*
Narsinh et al., 2011, Molecular therapy, vol. 9, No. 4, pp. 635-638.*
Bellin et al., 2012, Nature reviews/Molecular Cell Biology, vol. 13, p. 713-726.*
Burridge et al., 2011, PLoS One, vol. 6, No. 4, e18293, p. 1-16.*
International Search Report dated Dec. 13, 2016, in PCT/JP2016/077353.
Angelotti et al., "Characterization of Renal Progenitors Committed Toward Tubular Lineage and Their Regenerative Potential in Renal Tubular Injury," Stem Cells, 2012, 30:1714-1725.
Da Sacco et al., "Human Amniotic Fluid as a Potential New Source of Organ Specific Precursor Cells for Future Regenerative Medicine Applications," The Journal of Urology, Mar. 2010, 183:1193-1200.
Harari-Steinberg et al., "Identification of human nephron progenitors capable of generation of kidney structures and functional repair of chronic renal disease," EMBO Molecular Medicine, 2013, 5:1556-1568.

(Continued)

*Primary Examiner* — Shin Lin Chen

(74) *Attorney, Agent, or Firm* — Foley & Lardner LLP

(57) ABSTRACT

A method for acquiring and producing high-purity renal progenitor cells from a renal progenitor cell population into which pluripotent stem cells are induced to differentiate, by identifying a cell surface antigen marker specific to renal progenitor cells. The disclosed method may include, for example, the steps of:

(i) culturing the pluripotent stem cells under conditions that induce differentiation into renal progenitor cells; and (ii) sorting a cell population from the cells obtained at step (i), by using at least one cell surface marker selected from the group consisting of CD9(−), CD55(−), CD106(+), CD140a(+), CD140b(+), CD165(+), CD271(+) and CD326(−).

5 Claims, 7 Drawing Sheets
(3 of 7 Drawing Sheet(s) Filed in Color)
Specification includes a Sequence Listing.

(56) References Cited

OTHER PUBLICATIONS

Kobayashi et al., "Six2 Defines and Regulates a Multipotent Self-Renewing Nephron Progenitor Population throughout Mammalian Kidney Development," Cell Stem Cell, Aug. 7, 2008, 3:169-181.
Mae et al., "Combination of small molecules enhances differentiation of mouse embryonic stem cells into intermediate mesoderm through BMP7-positive cells," Biochemical and Biophysical Research Communications, 2010, 393:877-882.
Mae et al., "Monitoring and robust induction of nephrogenic intermediate mesoderm from human pluripotent stem cells," Nature Communications, Jan. 22, 2013, 4:1367, 1-11, with 22 pages of Supplementary Information.
Metsuyanim et al., "Expression of Stem Cell Markers in the Human Fetal Kidney," PLoS one, Aug. 21, 2009, (8)4:e6709, 1-15.
Sallustio et al., "Human renal stem/progenitor cells repair tubular epithelial cell injury through TLR2-driven inhibin-A and microvesicle-shuttled decorin," Kidney International, 2013, 83:392-403.
Shiraki et al., "Identification of DAF1/CD55, a Novel Definitive Endoderm Marker," Cell Structure and Function, 2010, 35:73-80.
Taguchi et al., "Redefining the in Vivo Origin of Metanephric Nephron Progenitors Enables Generation of Complex Kidney Structures from Pluripotent Stem Cells," Cell Stem Cell, Jan. 2, 2014, 14:53-67.
Toyohara et al., "Cell Therapy Using Human Induced Pluripotent Stem Cell-Derived Renal Progenitors Ameliorates Acute Kidney Injury in Mice," Stem Cells Translational Medicine, 2015, 4:980-992.
Velagapudi et al., "Reciprocal Induction of Simple Organogenesis by Mouse Kidney Progenitor Cells in Three-Dimensional Co-Culture," The American Journal of Pathology, Feb. 2012, 180(2):819-830.
Wang et al., "Induced pluripotent stem cell lines derived from human gingival fibroblasts and periodontal ligament fibroblasts," J. Periodont. Res., 2011, 46:437-447.
Hoshina et al: "Development of new method to enrich human iPSC-derived renal progenitors using cell surface markers," Scientific Reports, Apr. 2018, 8:6375 (12 pages).
Supplementary European Search Report dated Mar. 29, 2019 in EP 16844526.0.

* cited by examiner

[FIG. 1]
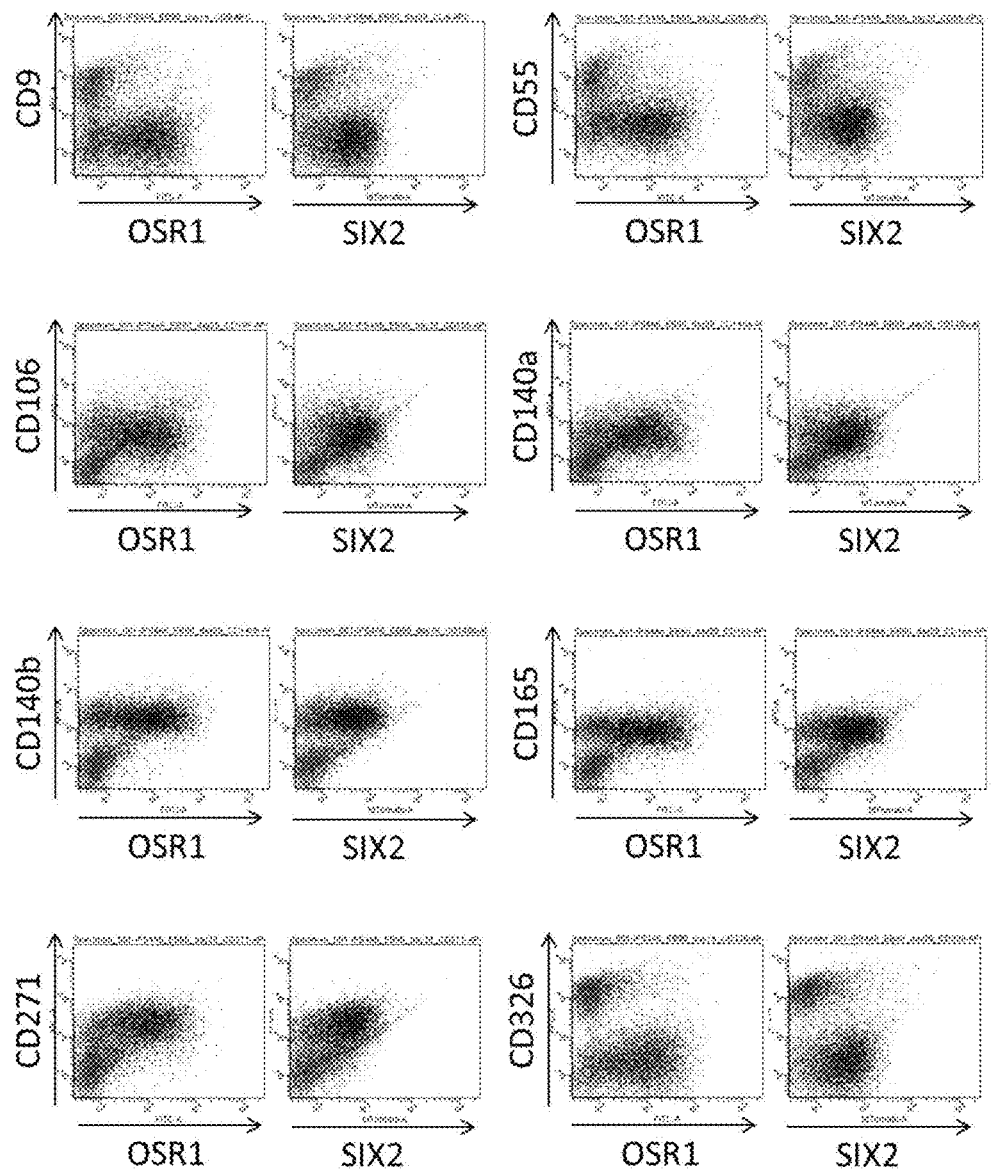

[FIG. 2]
A.
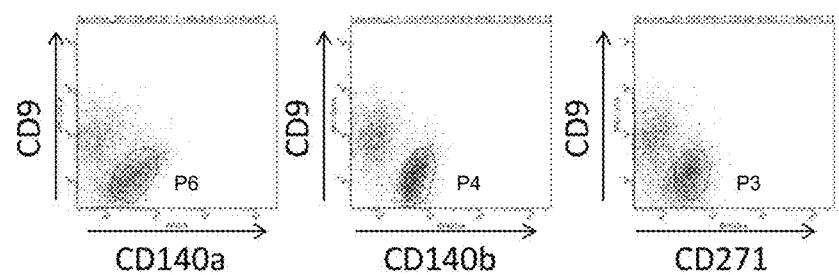
B.
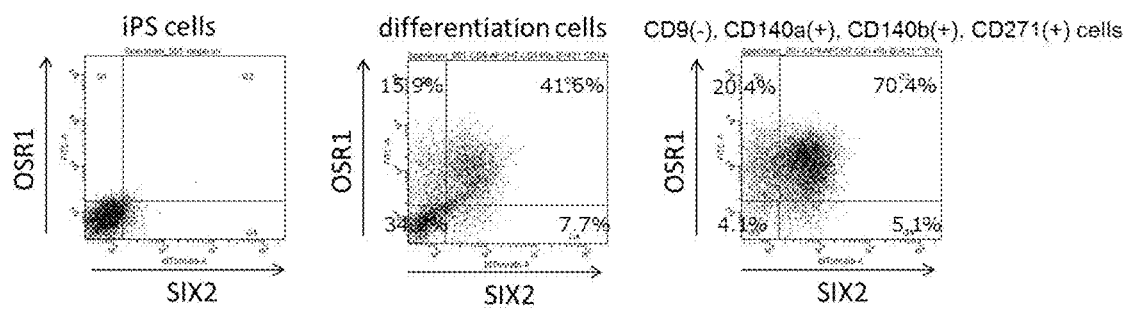

[FIG. 3]
A.
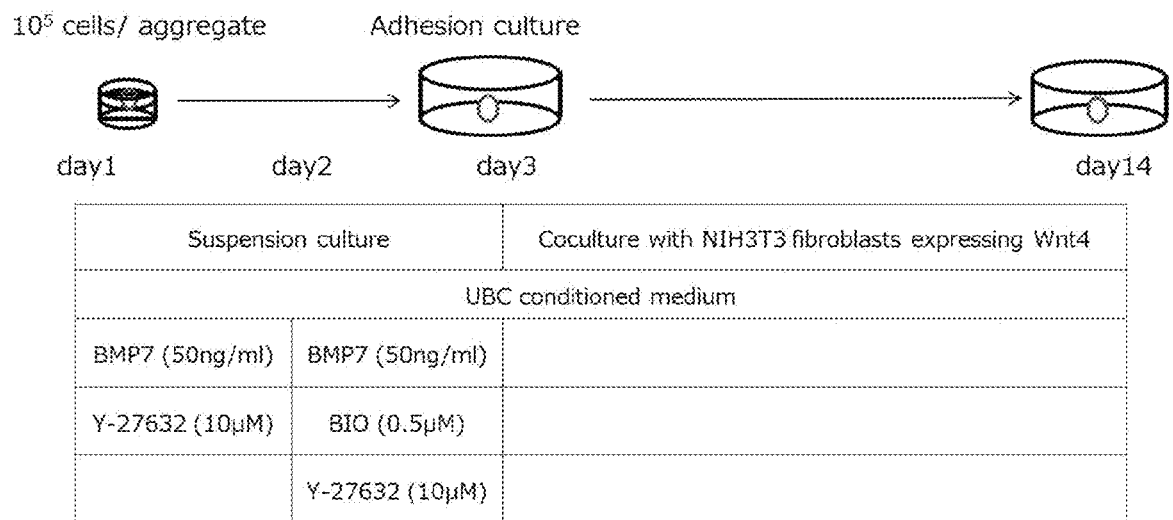
B.
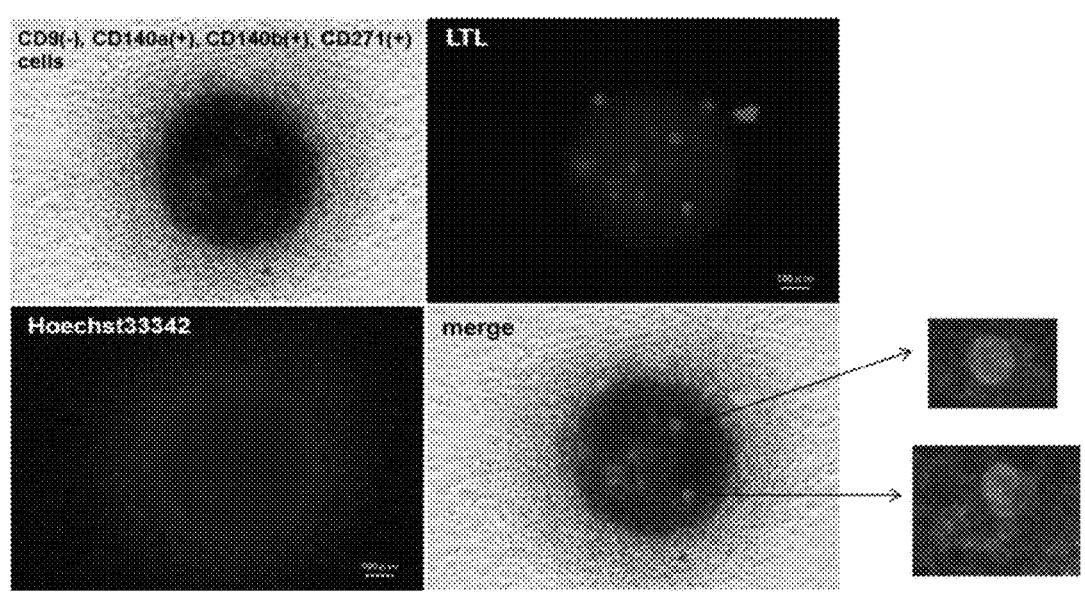

[FIG. 4]

|  | OSR1+,SIX2- | OSR1-,SIX2+ | OSR1+,SIX2+ | OSR1-,SIX2- |
|---|---|---|---|---|
| 1. CD9-,CD140a+,CD140b+,CD271+ | 17.0 | 6.8 | 72.3 | 3.9 |
| 2. CD9-,CD140a+,CD140b+,CD106+ | 19.1 | 8.9 | 65.6 | 6.4 |
| 3. CD9-,CD140a+,CD140b+,CD165+ | 17.5 | 16.0 | 52.6 | 13.9 |
| 4. CD9-,CD106+,CD140b+,CD271+ | 8.9 | 18.5 | 69.3 | 3.4 |
| 5. CD9-,CD165+CD140b+,CD271+ | 11.2 | 7.9 | 75.7 | 5.2 |
| 6. CD9-,CD140a+CD106+,CD271+ | 13.0 | 9.6 | 72.8 | 4.6 |
| 7. CD9-,CD140a+CD165+,CD271+ | 10.6 | 7.3 | 77.5 | 4.6 |
| 8. CD9-,CD106+,CD165+,CD140a+ | 9.7 | 17.2 | 67.8 | 5.3 |
| 9. CD9-,CD106+,CD165+,CD140b+ | 7.1 | 32.0 | 50.1 | 10.8 |
| 10. CD9-,CD106+,CD165+,CD271+ | 8.0 | 19.5 | 66.6 | 5.9 |
| 11. CD55-,CD140a+,CD140b+,CD271+ | 7.8 | 13.8 | 73.1 | 5.4 |
| 12. CD326-,CD140a+,CD140b+,CD271+ | 5.9 | 18.2 | 71.1 | 4.8 |

[FIG. 5]

| Surface antigen combination | Percentage of OSR1+SIX2+cells in unsorted differentiated cell population | Percentage of OSR1+SIX2+cells in cell population collected using each cell surface marker combination | Percentage of cells demarcated by each cell surface marker combination in unsorted cell population | Percentage of the number of OSR1+SIX2+cells collected using each cell surface marker combination with respect to the number of unsorted cells |
|---|---|---|---|---|
| CD9-, CD140a+ | 40.2 | 68.4 | 22.6 | 15.5 |
| CD9-, CD140b+ | 40.2 | 63.4 | 46.9 | 29.7 |
| CD9-, CD271+ | 40.2 | 68.5 | 31.5 | 21.6 |
| CD9-, CD140a+, CD140b+ | 40.2 | 69.1 | 21.4 | 14.8 |
| CD9-, CD140a+, CD271+ | 40.2 | 73.9 | 17.0 | 12.6 |
| CD9-, CD140b+, CD271+ | 40.2 | 71.3 | 29.0 | 20.7 |
| CD9-, CD140a+, CD140b+, CD271+ | 40.2 | 74.0 | 16.6 | 12.3 |
| CD140a+, CD140b+, CD271+ | 40.2 | 72.4 | 27.9 | 20.2 |

[FIG. 6]
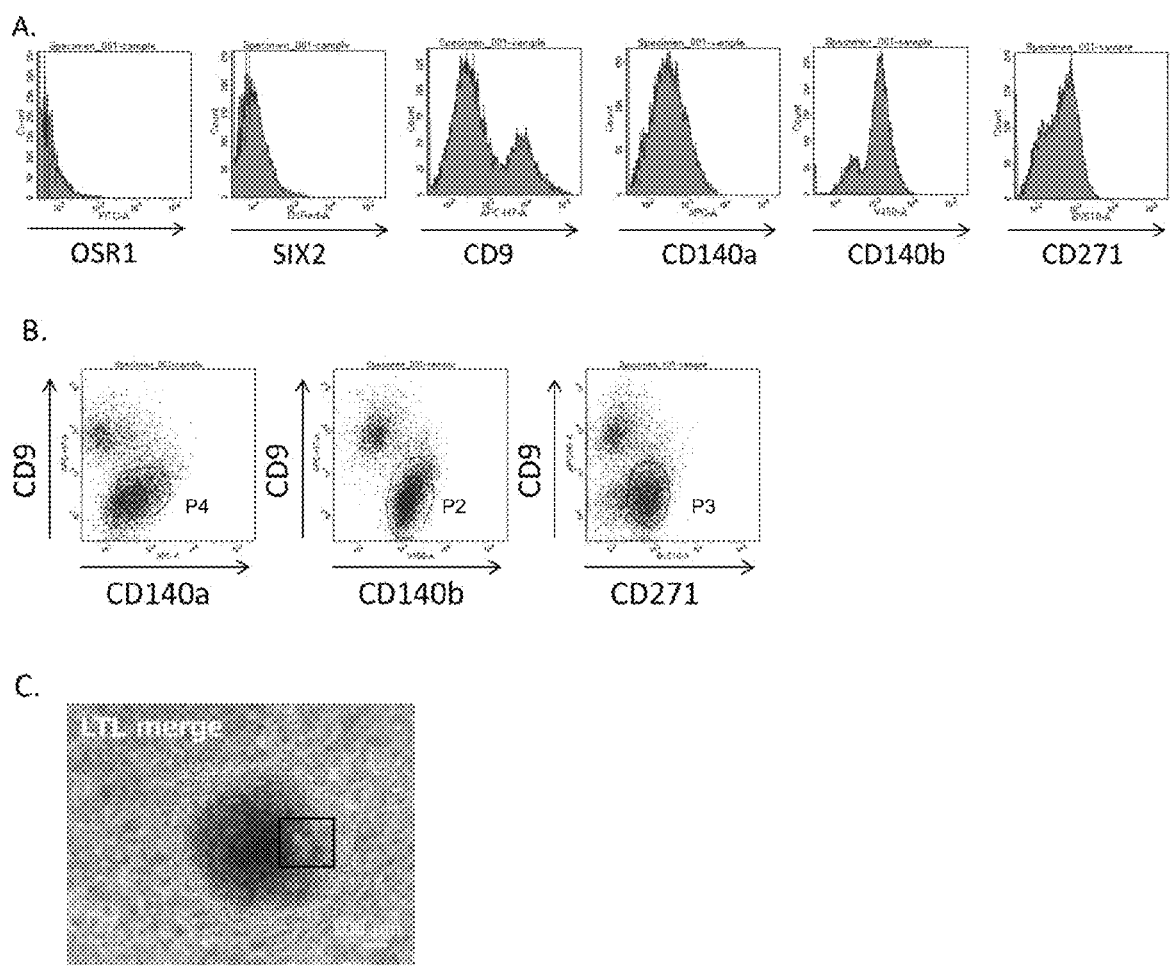

[FIG. 7]
A.
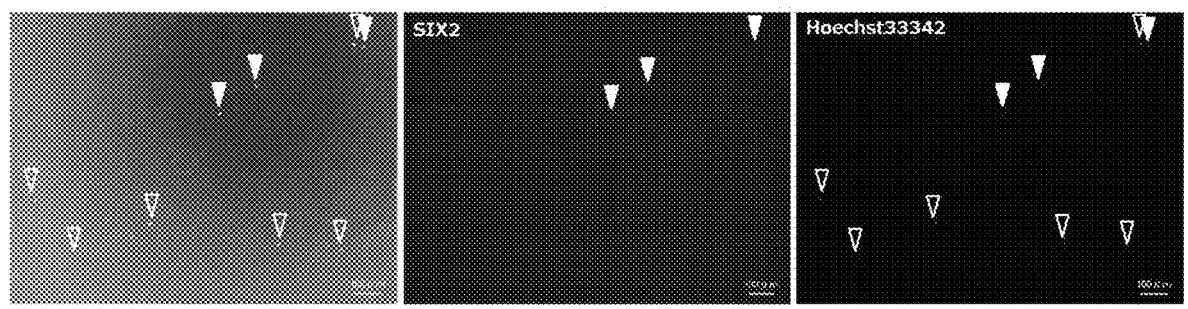
B.
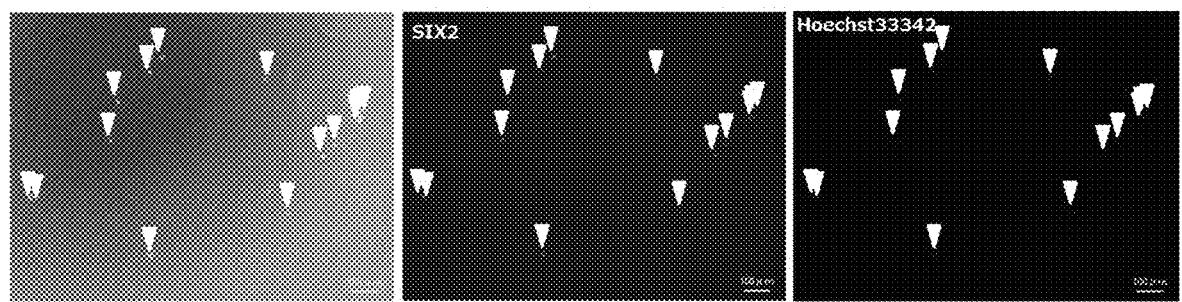

SEQUENCE LISTING

```
<160> NUMBER OF SEQ ID NOS: 15

<210> SEQ ID NO 1
<211> LENGTH: 1321
<212> TYPE: DNA
<213> ORGANISM: Homo sapiens
<220> FEATURE:
<221> NAME/KEY: CDS
<222> LOCATION: (185)..(871)
<300> PUBLICATION INFORMATION:
<308> DATABASE ACCESSION NUMBER: NM_001769.3
<309> DATABASE ENTRY DATE: 2015-03-15
<313> RELEVANT RESIDUES IN SEQ ID NO: (1)..(1321)

<400> SEQUENCE: 1
cttttcccgg cacatgcgca ccgcagcggg tcgcgcgccc taaggagtgg cactttttaa      60
```

```
aagtgcagcc ggagaccagc ctacagccgc ctgcatctgt atccagcgcc aggtcccgcc    120
agtcccagct gcgcgcgccc cccagtcccg cacccgttcg gcccaggcta agttagccct    180 cacc atg ccg gtc aaa gga ggc acc aag tgc atc aaa tac ctg ctg ttc    229
     Met Pro Val Lys Gly Gly Thr Lys Cys Ile Lys Tyr Leu Leu Phe
     1               5                   10                  15 gga ttt aac ttc atc ttc tgg ctt gcc ggg att gct gtc ctt gcc att    277
Gly Phe Asn Phe Ile Phe Trp Leu Ala Gly Ile Ala Val Leu Ala Ile
                20                  25                  30 gga cta tgg ctc cga ttc gac tct cag acc aag agc atc ttc gag caa    325
Gly Leu Trp Leu Arg Phe Asp Ser Gln Thr Lys Ser Ile Phe Glu Gln
            35                  40                  45 gaa act aat aat aat aat tcc agc ttc tac aca gga gtc tat att ctg    373
Glu Thr Asn Asn Asn Asn Ser Ser Phe Tyr Thr Gly Val Tyr Ile Leu
        50                  55                  60 atc gga gcc ggc gcc ctc atg atg ctg gtg ggc ttc ctg ggc tgc tgc    421
Ile Gly Ala Gly Ala Leu Met Met Leu Val Gly Phe Leu Gly Cys Cys
65                  70                  75 ggg gct gtg cag gag tcc cag tgc atg ctg gga ctg ttc ttc ggc ttc    469
Gly Ala Val Gln Glu Ser Gln Cys Met Leu Gly Leu Phe Phe Gly Phe
80                  85                  90                  95 ctc ttg gtg ata ttc gcc att gaa ata gct gcg gcc atc tgg gga tat    517
Leu Leu Val Ile Phe Ala Ile Glu Ile Ala Ala Ala Ile Trp Gly Tyr
                100                 105                 110 tcc cac aag gat gag gtg att aag gaa gtc cag gag ttt tac aag gac    565
Ser His Lys Asp Glu Val Ile Lys Glu Val Gln Glu Phe Tyr Lys Asp
            115                 120                 125 acc tac aac aag ctg aaa acc aag gat gag ccc cag cgg gaa acg ctg    613
Thr Tyr Asn Lys Leu Lys Thr Lys Asp Glu Pro Gln Arg Glu Thr Leu
        130                 135                 140 aaa gcc atc cac tat gcg ttg aac tgc tgt ggt ttg gct ggg ggc gtg    661
Lys Ala Ile His Tyr Ala Leu Asn Cys Cys Gly Leu Ala Gly Gly Val
    145                 150                 155 gaa cag ttt atc tca gac atc tgc ccc aag aag gac gta ctc gaa acc    709
Glu Gln Phe Ile Ser Asp Ile Cys Pro Lys Lys Asp Val Leu Glu Thr
160                 165                 170                 175 ttc acc gtg aag tcc tgt cct gat gcc atc aaa gag gtc ttc gac aat    757
Phe Thr Val Lys Ser Cys Pro Asp Ala Ile Lys Glu Val Phe Asp Asn
                180                 185                 190 aaa ttc cac atc atc ggc gca gtg ggc atc ggc att gcc gtg gtc atg    805
Lys Phe His Ile Ile Gly Ala Val Gly Ile Gly Ile Ala Val Val Met
            195                 200                 205 ata ttt ggc atg atc ttc agt atg atc ttg tgc tgt gct atc cgc agg    853
Ile Phe Gly Met Ile Phe Ser Met Ile Leu Cys Cys Ala Ile Arg Arg
        210                 215                 220 aac cgc gag atg gtc tag agtcagctta catccctgag caggaaagtt           901
Asn Arg Glu Met Val
    225 tacccatgaa gattggtggg atttttttgtt tgtttgtttt gttttgtttg ttgtttgttg    961 tttgtttttt tgccactaat tttagtattc attctgcatt gctagataaa agctgaagtt   1021 actttatgtt tgtctttttaa tgcttcattc aatattgaca tttgtagttg agcgggggt   1081 ttggtttgct ttggtttata ttttttcagt tgtttgtttt tgcttgttat attaagcaga   1141 aatcctgcaa tgaaaggtac tatatttgct agactctaga caagatattg tacataaaag   1201 aatttttttg tctttaaata gatacaaatg tctatcaact ttaatcaagt tgtaacttat   1261 attgaagaca atttgataca taataaaaaa ttatgacaat gtcctggact ggtaaaaaaa   1321
```

<210> SEQ ID NO 2
<211> LENGTH: 228
<212> TYPE: PRT
<213> ORGANISM: Homo sapiens

<400> SEQUENCE: 2

```
Met Pro Val Lys Gly Gly Thr Lys Cys Ile Lys Tyr Leu Leu Phe Gly
 1               5                  10                  15

Phe Asn Phe Ile Phe Trp Leu Ala Gly Ile Ala Val Leu Ala Ile Gly
             20                  25                  30

Leu Trp Leu Arg Phe Asp Ser Gln Thr Lys Ser Ile Phe Glu Gln Glu
         35                  40                  45

Thr Asn Asn Asn Ser Ser Phe Tyr Thr Gly Val Tyr Ile Leu Ile
     50                  55                  60

Gly Ala Gly Ala Leu Met Met Leu Val Gly Phe Leu Gly Cys Cys Gly
 65                  70                  75                  80

Ala Val Gln Glu Ser Gln Cys Met Leu Gly Leu Phe Phe Gly Phe Leu
                 85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225
```

<210> SEQ ID NO 3
<211> LENGTH: 2796
<212> TYPE: DNA
<213> ORGANISM: Homo sapiens
<220> FEATURE:
<221> NAME/KEY: CDS
<222> LOCATION: (295)..(1140)
<300> PUBLICATION INFORMATION:
<308> DATABASE ACCESSION NUMBER: NM_000574.4
<309> DATABASE ENTRY DATE: 2015-03-15
<313> RELEVANT RESIDUES IN SEQ ID NO: (1)..(2796)

<400> SEQUENCE: 3

| | |
|---|---|
| agcgagctcc tcctccttcc cctccccact ctccccgagt ctagggcccc cggggcgtat | 60 |
| gacgccggag ccctctgacc gcacctctga ccacaacaaa ccctactcc accgtcttg | 120 |
| tttgtcccac ccttggtgac gcagagcccc agcccagacc ccgcccaaag cactcattta | 180 |
| actggtattg cggagccacg aggcttctgc ttactgcaac tcgctccggc cgctgggcgt | 240 |
| agctgcgact cggcggagtc ccggcggcgc gtccttgttc taacccggcg cgcc atg | 297 |
| | Met |
| | 1 |

```
acc gtc gcg cgg ccg agc gtg ccc gcg gcg ctg ccc ctc ctc ggg gag      345
Thr Val Ala Arg Pro Ser Val Pro Ala Ala Leu Pro Leu Leu Gly Glu
        5                  10                  15 ctg ccc cgg ctg ctg ctg ctg gtg ctg ttg tgc ctg ccg gcc gtg tgg      393
Leu Pro Arg Leu Leu Leu Leu Val Leu Leu Cys Leu Pro Ala Val Trp
            20                  25                  30 ggt gac tgt ggc ctt ccc cca gat gta cct aat gcc cag cca gct ttg      441
Gly Asp Cys Gly Leu Pro Pro Asp Val Pro Asn Ala Gln Pro Ala Leu
        35                  40                  45 gaa ggc cgt aca agt ttt ccc gag gat act gta ata acg tac aaa tgt      489
Glu Gly Arg Thr Ser Phe Pro Glu Asp Thr Val Ile Thr Tyr Lys Cys
 50                  55                  60                  65 gaa gaa agc ttt gtg aaa att cct ggc gag aag gac tca gtg atc tgc      537
Glu Glu Ser Phe Val Lys Ile Pro Gly Glu Lys Asp Ser Val Ile Cys
                     70                  75                  80 ctt aag ggc agt caa tgg tca gat att gaa gag ttc tgc aat cgt agc      585
Leu Lys Gly Ser Gln Trp Ser Asp Ile Glu Glu Phe Cys Asn Arg Ser
                85                  90                  95 tgc gag gtg cca aca agg cta aat tct gca tcc ctc aaa cag cct tat      633
Cys Glu Val Pro Thr Arg Leu Asn Ser Ala Ser Leu Lys Gln Pro Tyr
            100                 105                 110 atc act cag aat tat ttt cca gtc ggt act gtt gtg gaa tat gag tgc      681
Ile Thr Gln Asn Tyr Phe Pro Val Gly Thr Val Val Glu Tyr Glu Cys
        115                 120                 125 cgt cca ggt tac aga aga gaa cct tct cta tca cca aaa cta act tgc      729
Arg Pro Gly Tyr Arg Arg Glu Pro Ser Leu Ser Pro Lys Leu Thr Cys
130                 135                 140                 145 ctt cag aat tta aaa tgg tcc aca gca gtc gaa ttt tgt aaa aag aaa      777
Leu Gln Asn Leu Lys Trp Ser Thr Ala Val Glu Phe Cys Lys Lys Lys
                150                 155                 160 tca tgc cct aat ccg gga gaa ata cga aat ggt cag att gat gta cca      825
Ser Cys Pro Asn Pro Gly Glu Ile Arg Asn Gly Gln Ile Asp Val Pro
            165                 170                 175 ggt ggc ata tta ttt ggt gca acc atc tcc ttc tca tgt aac aca ggg      873
Gly Gly Ile Leu Phe Gly Ala Thr Ile Ser Phe Ser Cys Asn Thr Gly
        180                 185                 190 tac aaa tta ttt ggc tcg act tct agt ttt tgt ctt att tca ggc agc      921
Tyr Lys Leu Phe Gly Ser Thr Ser Ser Phe Cys Leu Ile Ser Gly Ser
    195                 200                 205 tct gtc cag tgg agt gac ccg ttg cca gag tgc aga gaa att tat tgt      969
Ser Val Gln Trp Ser Asp Pro Leu Pro Glu Cys Arg Glu Ile Tyr Cys
210                 215                 220                 225 cca gca cca cca caa att gac aat gga ata att caa ggg gaa cgt gac      1017
Pro Ala Pro Pro Gln Ile Asp Asn Gly Ile Ile Gln Gly Glu Arg Asp
                230                 235                 240 cat tat gga tat aga cag tct gta acg tat gca tgt aat aaa gga ttc      1065
His Tyr Gly Tyr Arg Gln Ser Val Thr Tyr Ala Cys Asn Lys Gly Phe
            245                 250                 255 acc atg att gga gag cac tct att tat tgt act gtg aat aat gat gaa      1113
Thr Met Ile Gly Glu His Ser Ile Tyr Cys Thr Val Asn Asn Asp Glu
        260                 265                 270 gga gag tgg agt ggc cca cca cct gaa tgcagaggaa aatctctaac            1160
Gly Glu Trp Ser Gly Pro Pro Pro Glu
    275                 280 ttccaaggtc ccaccaacag ttcagaaacc taccacagta aatgttccaa ctacagaagt    1220
ctcaccaact tctcagaaaa ccaccacaaa aaccaccaca ccaaatgctc aagcaacacg    1280
gagtacacct gtttccagga caaccaagca ttttcatgaa acaaccccaa ataaggaag     1340
```

```
tggaaccact tcaggtacta cccgtcttct atctgggcac acgtgtttca cgttgacagg    1400
tttgcttggg acgctagtaa ccatgggctt gctgacttag ccaaagaaga gttaagaaga    1460
aaatacacac aagtatacag actgttccta gtttcttaga cttatctgca tattggataa    1520
aataaatgca attgtgctct tcatttagga tgctttcatt gtctttaaga tgtgttagga    1580
atgtcaacag agcaaggaga aaaaaggcag tcctggaatc acattcttag cacacctaca    1640
cctcttgaaa atagaacaac ttgcagaatt gagagtgatt cctttcctaa agtgtaaga    1700 aagcatagag atttgttcgt atttagaatg ggatcacgag aaaagagaa ggaaagtgat    1760 ttttttccac aagatctgta atgttatttc cacttataaa ggaaataaaa aatgaaaaac    1820
attatttgga tatcaaaagc aaataaaaac ccaattcagt ctcttctaag caaaattgct    1880
aaagagagat gaaccacatt ataaagtaat ctttggctgt aaggcatttt catctttcct    1940
tcgggttggc aaaatatttt aaaggtaaaa catgctggtg aaccagggg gttgatggtg    2000 ataaggagg aatatagaat gaaagactga atcttccttt gttgcacaaa tagagtttgg    2060
aaaaagcctg tgaaaggtgt cttctttgac ttaatgtctt taaaagtatc cagagatact    2120
acaatattaa cataagaaaa gattatatat tatttctgaa tcgagatgtc catagtcaaa    2180
tttgtaaatc ttattctttt gtaatatttta tttatttta tttatgacag tgaacattct    2240
gattttacat gtaaaacaag aaaagttgaa gaagatatgt gaagaaaaat gtattttttcc    2300 taaatagaaa taaatgatcc catttttttgg tatcatgtag tatgtgaaat ttattcttaa    2360
acgtgactac tttatttcta aataagaaat tccctacctg cttcctacaa gcagttcaga    2420
atgccatgcc ttggttgtcc tagtgtgaat aattttcagc tactttaaaa ttatattgta    2480
ctttctcaag catgtcatat cctttcctat tagagtatct atattacttg ttactgattt    2540
acctgaaggc aatctgatta atttctaggt ttttaccata ttcttgtcat cttgccaatt    2600 acatttaag tgttagacta gactaagatg tactagttgt atagaatata actagattta    2660
ttatggcaat gtttatttttg tcattttgct tcatctgttt tgttgttgaa gtactttaaa    2720
tttcatacgt tcatggcatt tcactgtaaa gactttaatg tgtatttctt aaaataaaac    2780
tttttttcct ccttaa                                                    2796
```

<210> SEQ ID NO 4
<211> LENGTH: 282
<212> TYPE: PRT
<213> ORGANISM: Homo sapiens

<400> SEQUENCE: 4

Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
                20                  25                  30

Trp Gly Asp Cys Gly Leu Pro Pro Asp Val Pro Asn Ala Gln Pro Ala
            35                  40                  45

Leu Glu Gly Arg Thr Ser Phe Pro Glu Asp Thr Val Ile Thr Tyr Lys
        50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
                100                 105                 110

```
Tyr Ile Thr Gln Asn Tyr Phe Pro Val Gly Thr Val Val Glu Tyr Glu
            115                 120                 125

Cys Arg Pro Gly Tyr Arg Arg Glu Pro Ser Leu Ser Pro Lys Leu Thr
130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
        195                 200                 205

Ser Ser Val Gln Trp Ser Asp Pro Leu Pro Glu Cys Arg Glu Ile Tyr
    210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Glu
        275                 280

<210> SEQ ID NO 5
<211> LENGTH: 3220
<212> TYPE: DNA
<213> ORGANISM: Homo sapiens
<220> FEATURE:
<221> NAME/KEY: CDS
<222> LOCATION: (222)..(2441)
<300> PUBLICATION INFORMATION:
<308> DATABASE ACCESSION NUMBER: NM_001078.3
<309> DATABASE ENTRY DATE: 2015-03-15
<313> RELEVANT RESIDUES IN SEQ ID NO: (1)..(3220)

<400> SEQUENCE: 5 aaacttttt  ccctggctct  gccctgggtt  tccccttgaa  gggatttccc  tccgcctctg      60
caacaagacc  ctttataaag  cacagacttt  ctatttcact  ccgcggtatc  tgcatcgggc     120
ctcactggct  tcaggagctg  aatacccctcc caggcacaca  caggtgggac  acaaataagg     180
gttttggaac  cactattttc  tcatcacgac  agcaacttaa a atg cct ggg aag atg       236
                                                 Met Pro Gly Lys Met
                                                  1               5 gtc gtg atc ctt gga gcc tca aat ata ctt tgg ata atg ttt gca gct           284
Val Val Ile Leu Gly Ala Ser Asn Ile Leu Trp Ile Met Phe Ala Ala
             10                  15                  20 tct caa gct ttt aaa atc gag acc acc cca gaa tct aga tat ctt gct           332
Ser Gln Ala Phe Lys Ile Glu Thr Thr Pro Glu Ser Arg Tyr Leu Ala
         25                  30                  35 cag att ggt gac tcc gtc tca ttg act tgc agc acc aca ggc tgt gag           380
Gln Ile Gly Asp Ser Val Ser Leu Thr Cys Ser Thr Thr Gly Cys Glu
     40                  45                  50 tcc cca ttt ttc tct tgg aga acc cag ata gat agt cca ctg aat ggg           428
Ser Pro Phe Phe Ser Trp Arg Thr Gln Ile Asp Ser Pro Leu Asn Gly
 55                  60                  65 aag gtg acg aat gag ggg acc aca tct acg ctg aca atg aat cct gtt           476
Lys Val Thr Asn Glu Gly Thr Thr Ser Thr Leu Thr Met Asn Pro Val
70                  75                  80                  85 agt ttt ggg aac gaa cac tct tac ctg tgc aca gca act tgt gaa tct           524
```

|  |  |  |  |  |  |  |  |  |  |  |  |  |  |
|--|--|--|--|--|--|--|--|--|--|--|--|--|--|
|Ser|Phe|Gly|Asn|Glu|His|Ser|Tyr|Leu|Cys|Thr|Ala|Thr|Cys|Glu|Ser|
|   |   |   |   |90 |   |   |   |95 |   |   |   |   |100|   |   |

```
agg aaa ttg gaa aaa gga atc cag gtg gag atc tac tct ttt cct aag    572
Arg Lys Leu Glu Lys Gly Ile Gln Val Glu Ile Tyr Ser Phe Pro Lys
        105                 110                 115 gat cca gag att cat ttg agt ggc cct ctg gag gct ggg aag ccg atc    620
Asp Pro Glu Ile His Leu Ser Gly Pro Leu Glu Ala Gly Lys Pro Ile
        120                 125                 130 aca gtc aag tgt tca gtt gct gat gta tac cca ttt gac agg ctg gag    668
Thr Val Lys Cys Ser Val Ala Asp Val Tyr Pro Phe Asp Arg Leu Glu
        135                 140                 145 ata gac tta ctg aaa gga gat cat ctc atg aag agt cag gaa ttt ctg    716
Ile Asp Leu Leu Lys Gly Asp His Leu Met Lys Ser Gln Glu Phe Leu
150                 155                 160                 165 gag gat gca gac agg aag tcc ctg gaa acc aag agt ttg gaa gta acc    764
Glu Asp Ala Asp Arg Lys Ser Leu Glu Thr Lys Ser Leu Glu Val Thr
                170                 175                 180 ttt act cct gtc att gag gat att gga aaa gtt ctt gtt tgc cga gct    812
Phe Thr Pro Val Ile Glu Asp Ile Gly Lys Val Leu Val Cys Arg Ala
            185                 190                 195 aaa tta cac att gat gaa atg gat tct gtg ccc aca gta agg cag gct    860
Lys Leu His Ile Asp Glu Met Asp Ser Val Pro Thr Val Arg Gln Ala
        200                 205                 210 gta aaa gaa ttg caa gtc tac ata tca ccc aag aat aca gtt att tct    908
Val Lys Glu Leu Gln Val Tyr Ile Ser Pro Lys Asn Thr Val Ile Ser
        215                 220                 225 gtg aat cca tcc aca aag ctg caa gaa ggt ggc tct gtg acc atg acc    956
Val Asn Pro Ser Thr Lys Leu Gln Glu Gly Gly Ser Val Thr Met Thr
230                 235                 240                 245 tgt tcc agc gag ggt cta cca gct cca gag att ttc tgg agt aag aaa   1004
Cys Ser Ser Glu Gly Leu Pro Ala Pro Glu Ile Phe Trp Ser Lys Lys
                250                 255                 260 tta gat aat ggg aat cta cag cac ctt tct gga aat gca act ctc acc   1052
Leu Asp Asn Gly Asn Leu Gln His Leu Ser Gly Asn Ala Thr Leu Thr
            265                 270                 275 tta att gct atg agg atg gaa gat tct gga att tat gtg tgt gaa gga   1100
Leu Ile Ala Met Arg Met Glu Asp Ser Gly Ile Tyr Val Cys Glu Gly
        280                 285                 290 gtt aat ttg att ggg aaa aac aga aaa gag gtg gaa tta att gtt caa   1148
Val Asn Leu Ile Gly Lys Asn Arg Lys Glu Val Glu Leu Ile Val Gln
        295                 300                 305 gag aaa cca ttt act gtt gag atc tcc cct gga ccc cgg att gct gct   1196
Glu Lys Pro Phe Thr Val Glu Ile Ser Pro Gly Pro Arg Ile Ala Ala
310                 315                 320                 325 cag att gga gac tca gtc atg ttg aca tgt agt gtc atg ggc tgt gaa   1244
Gln Ile Gly Asp Ser Val Met Leu Thr Cys Ser Val Met Gly Cys Glu
                330                 335                 340 tcc cca tct ttc tcc tgg aga acc cag ata gac agc cct ctg agc ggg   1292
Ser Pro Ser Phe Ser Trp Arg Thr Gln Ile Asp Ser Pro Leu Ser Gly
            345                 350                 355 aag gtg agg agt gag ggg acc aat tcc acg ctg acc ctg agc cct gtg   1340
Lys Val Arg Ser Glu Gly Thr Asn Ser Thr Leu Thr Leu Ser Pro Val
        360                 365                 370 agt ttt gag aac gaa cac tct tat ctg tgc aca gtg act tgt gga cat   1388
Ser Phe Glu Asn Glu His Ser Tyr Leu Cys Thr Val Thr Cys Gly His
        375                 380                 385 aag aaa ctg gaa aag gga atc cag gtg gag ctc tac tca ttc cct aga   1436
Lys Lys Leu Glu Lys Gly Ile Gln Val Glu Leu Tyr Ser Phe Pro Arg
390                 395                 400                 405
```

```
gat cca gaa atc gag atg agt ggt ggc ctc gtg aat ggg agc tct gtc      1484
Asp Pro Glu Ile Glu Met Ser Gly Gly Leu Val Asn Gly Ser Ser Val
            410                 415                 420 act gta agc tgc aag gtt cct agc gtg tac ccc ctt gac cgg ctg gag      1532
Thr Val Ser Cys Lys Val Pro Ser Val Tyr Pro Leu Asp Arg Leu Glu
        425                 430                 435 att gaa tta ctt aag ggg gag act att ctg gag aat ata gag ttt ttg      1580
Ile Glu Leu Leu Lys Gly Glu Thr Ile Leu Glu Asn Ile Glu Phe Leu
    440                 445                 450 gag gat acg gat atg aaa tct cta gag aac aaa agt ttg gaa atg acc      1628
Glu Asp Thr Asp Met Lys Ser Leu Glu Asn Lys Ser Leu Glu Met Thr
455                 460                 465 ttc atc cct acc att gaa gat act gga aaa gct ctt gtt tgt cag gct      1676
Phe Ile Pro Thr Ile Glu Asp Thr Gly Lys Ala Leu Val Cys Gln Ala
470                 475                 480                 485 aag tta cat att gat gac atg gaa ttc gaa ccc aaa caa agg cag agt      1724
Lys Leu His Ile Asp Asp Met Glu Phe Glu Pro Lys Gln Arg Gln Ser
            490                 495                 500 acg caa aca ctt tat gtc aat gtt gcc ccc aga gat aca acc gtc ttg      1772
Thr Gln Thr Leu Tyr Val Asn Val Ala Pro Arg Asp Thr Thr Val Leu
        505                 510                 515 gtc agc cct tcc tcc atc ctg gag gaa ggc agt tct gtg aat atg aca      1820
Val Ser Pro Ser Ser Ile Leu Glu Glu Gly Ser Ser Val Asn Met Thr
    520                 525                 530 tgc ttg agc cag ggc ttt cct gct ccg aaa atc ctg tgg agc agg cag      1868
Cys Leu Ser Gln Gly Phe Pro Ala Pro Lys Ile Leu Trp Ser Arg Gln
535                 540                 545 ctc cct aac ggg gag cta cag cct ctt tct gag aat gca act ctc acc      1916
Leu Pro Asn Gly Glu Leu Gln Pro Leu Ser Glu Asn Ala Thr Leu Thr
550                 555                 560                 565 tta att tct aca aaa atg gaa gat tct ggg gtt tat tta tgt gaa gga      1964
Leu Ile Ser Thr Lys Met Glu Asp Ser Gly Val Tyr Leu Cys Glu Gly
            570                 575                 580 att aac cag gct gga aga agc aga aag gaa gtg gaa tta att atc caa      2012
Ile Asn Gln Ala Gly Arg Ser Arg Lys Glu Val Glu Leu Ile Ile Gln
        585                 590                 595 gtt act cca aaa gac ata aaa ctt aca gct ttt cct tct gag agt gtc      2060
Val Thr Pro Lys Asp Ile Lys Leu Thr Ala Phe Pro Ser Glu Ser Val
    600                 605                 610 aaa gaa gga gac act gtc atc atc tct tgt aca tgt gga aat gtt cca      2108
Lys Glu Gly Asp Thr Val Ile Ile Ser Cys Thr Cys Gly Asn Val Pro
615                 620                 625 gaa aca tgg ata atc ctg aag aaa aaa gcg gag aca gga gac aca gta      2156
Glu Thr Trp Ile Ile Leu Lys Lys Lys Ala Glu Thr Gly Asp Thr Val
630                 635                 640                 645 cta aaa tct ata gat ggc gcc tat acc atc cga aag gcc cag ttg aag      2204
Leu Lys Ser Ile Asp Gly Ala Tyr Thr Ile Arg Lys Ala Gln Leu Lys
            650                 655                 660 gat gcg gga gta tat gaa tgt gaa tct aaa aac aaa gtt ggc tca caa      2252
Asp Ala Gly Val Tyr Glu Cys Glu Ser Lys Asn Lys Val Gly Ser Gln
        665                 670                 675 tta aga agt tta aca ctt gat gtt caa gga aga gaa aac aac aaa gac      2300
Leu Arg Ser Leu Thr Leu Asp Val Gln Gly Arg Glu Asn Asn Lys Asp
    680                 685                 690 tat ttt tct cct gag ctt ctc gtg ctc tat ttt gca tcc tcc tta ata      2348
Tyr Phe Ser Pro Glu Leu Leu Val Leu Tyr Phe Ala Ser Ser Leu Ile
695                 700                 705 ata cct gcc att gga atg ata att tac ttt gca aga aaa gcc aac atg      2396
Ile Pro Ala Ile Gly Met Ile Ile Tyr Phe Ala Arg Lys Ala Asn Met
710                 715                 720                 725
```

-continued

```
aag ggg tca tat agt ctt gta gaa gca cag aag tca aaa gtg tag        2441
Lys Gly Ser Tyr Ser Leu Val Glu Ala Gln Lys Ser Lys Val
            730                 735 ctaatgcttg atatgttcaa ctggagacac tatttatctg tgcaaatcct tgatactgct  2501
catcattcct tgagaaaaac aatgagctga gaggcagact tccctgaatg tattgaactt  2561
ggaaagaaat gcccatctat gtcccttgct gtgagcaaga agtcaaagta aaacttgctg  2621
cctgaagaac agtaactgcc atcaagatga gagaactgga ggagttcctt gatctgtata  2681
tacaataaca taatttgtac atatgtaaaa taaaattatg ccatagcaag attgcttaaa  2741
atagcaacac tctatattta gattgttaaa ataactagtg ttgcttggac tattataatt  2801
taatgcatgt taggaaaatt tcacattaat atttgctgac agctgacctt tgtcatcttt  2861
cttctatttt attcccttc acaaaatttt attcctatat agtttattga caataatttc  2921
aggttttgta aagatgccgg gttttatatt tttatagaca ataataagc aaagggagca   2981 ctgggttgac tttcaggtac taaatacctc aacctatggt ataatggttg actgggtttc  3041
tctgtatagt actggcatgg tacggagatg tttcacgaag tttgttcatc agactcctgt  3101
gcaactttcc caatgtggcc taaaaatgca acttctttt attttctttt gtaaatgttt   3161
aggttttttt gtatagtaaa gtgataattt ctggaattag aaaaaaaaaa aaaaaaaa    3220
```

<210> SEQ ID NO 6
<211> LENGTH: 739
<212> TYPE: PRT
<213> ORGANISM: Homo sapiens

<400> SEQUENCE: 6

```
Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
```

```
               210                 215                 220
Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
                260                 265                 270

Asn Ala Thr Leu Thr Leu Ile Ala Met Arg Met Glu Asp Ser Gly Ile
                275                 280                 285

Tyr Val Cys Glu Gly Val Asn Leu Ile Gly Lys Asn Arg Lys Glu Val
                290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
                340                 345                 350

Ser Pro Leu Ser Gly Lys Val Arg Ser Glu Gly Thr Asn Ser Thr Leu
                355                 360                 365

Thr Leu Ser Pro Val Ser Phe Glu Asn Glu His Ser Tyr Leu Cys Thr
                370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
                420                 425                 430

Leu Asp Arg Leu Glu Ile Glu Leu Leu Lys Gly Glu Thr Ile Leu Glu
                435                 440                 445

Asn Ile Glu Phe Leu Glu Asp Thr Asp Met Lys Ser Leu Glu Asn Lys
450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
                500                 505                 510

Asp Thr Thr Val Leu Val Ser Pro Ser Ser Ile Leu Glu Glu Gly Ser
                515                 520                 525

Ser Val Asn Met Thr Cys Leu Ser Gln Gly Phe Pro Ala Pro Lys Ile
                530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
                580                 585                 590

Glu Leu Ile Ile Gln Val Thr Pro Lys Asp Ile Lys Leu Thr Ala Phe
                595                 600                 605

Pro Ser Glu Ser Val Lys Glu Gly Asp Thr Val Ile Ile Ser Cys Thr
                610                 615                 620

Cys Gly Asn Val Pro Glu Thr Trp Ile Ile Leu Lys Lys Lys Ala Glu
625                 630                 635                 640
```

```
Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 7
<211> LENGTH: 6574
<212> TYPE: DNA
<213> ORGANISM: Homo sapiens
<220> FEATURE:
<221> NAME/KEY: CDS
<222> LOCATION: (332)..(3601)
<300> PUBLICATION INFORMATION:
<308> DATABASE ACCESSION NUMBER: NM_006206.4
<309> DATABASE ENTRY DATE: 2015-03-15
<313> RELEVANT RESIDUES IN SEQ ID NO: (1)..(6574)

<400> SEQUENCE: 7
aagagcaaaa agcgaaggcg caatctggac actgggagat tcggagcgca gggagtttga    60
gagaaacttt tattttgaag agaccaaggt tgagggggggg cttatttcct gacagctatt   120
tacttagagc aaatgattag ttttagaagg atggactata acattgaatc aattacaaaa   180
cgcggttttt gagcccatta ctgttggagc tacagggaga gaaacagagg aggagactgc   240
aagagatcat tggaggccgt gggcacgctc tttactccat gtgtgggaca ttcattgcgg   300
aataacatcg gaggagaagt tcccagagc t atg ggg act tcc cat ccg gcg        352
                                  Met Gly Thr Ser His Pro Ala
                                  1               5 ttc ctg gtc tta ggc tgt ctt ctc aca ggg ctg agc cta atc ctc tgc      400
Phe Leu Val Leu Gly Cys Leu Leu Thr Gly Leu Ser Leu Ile Leu Cys
        10                  15                  20 cag ctt tca tta ccc tct atc ctt cca aat gaa aat gaa aag gtt gtg      448
Gln Leu Ser Leu Pro Ser Ile Leu Pro Asn Glu Asn Glu Lys Val Val
    25                  30                  35 cag ctg aat tca tcc ttt tct ctg aga tgc ttt ggg gag agt gaa gtg      496
Gln Leu Asn Ser Ser Phe Ser Leu Arg Cys Phe Gly Glu Ser Glu Val
40                  45                  50                  55 agc tgg cag tac ccc atg tct gaa gaa gag agc tcc gat gtg gaa atc      544
Ser Trp Gln Tyr Pro Met Ser Glu Glu Glu Ser Ser Asp Val Glu Ile
                60                  65                  70 aga aat gaa gaa aac aac agc ggc ctt ttt gtg acg gtc ttg gaa gtg      592
Arg Asn Glu Glu Asn Asn Ser Gly Leu Phe Val Thr Val Leu Glu Val
            75                  80                  85 agc agt gcc tcg gcg gcc cac aca ggg ttg tac act tgc tat tac aac      640
Ser Ser Ala Ser Ala Ala His Thr Gly Leu Tyr Thr Cys Tyr Tyr Asn
        90                  95                  100 cac act cag aca gaa gag aat gag ctt gaa ggc agg cac att tac atc      688
His Thr Gln Thr Glu Glu Asn Glu Leu Glu Gly Arg His Ile Tyr Ile
    105                 110                 115 tat gtg cca gac cca gat gta gcc ttt gta cct cta gga atg acg gat      736
```

-continued

| | | | | | | | | | | | | | | | |
|---|---|---|---|---|---|---|---|---|---|---|---|---|---|---|---|
|Tyr|Val|Pro|Asp|Pro|Asp|Val|Ala|Phe|Val|Pro|Leu|Gly|Met|Thr|Asp|
|120| | | |125| | | | |130| | | | |135| |

```
tat tta gtc atc gtg gag gat gat gat tct gcc att ata cct tgt cgc      784
Tyr Leu Val Ile Val Glu Asp Asp Asp Ser Ala Ile Ile Pro Cys Arg
            140                 145                 150 aca act gat ccc gag act cct gta acc tta cac aac agt gag ggg gtg      832
Thr Thr Asp Pro Glu Thr Pro Val Thr Leu His Asn Ser Glu Gly Val
            155                 160                 165 gta cct gcc tcc tac gac agc aga cag ggc ttt aat ggg acc ttc act      880
Val Pro Ala Ser Tyr Asp Ser Arg Gln Gly Phe Asn Gly Thr Phe Thr
            170                 175                 180 gta ggg ccc tat atc tgt gag gcc acc gtc aaa gga aag aag ttc cag      928
Val Gly Pro Tyr Ile Cys Glu Ala Thr Val Lys Gly Lys Lys Phe Gln
            185                 190                 195 acc atc cca ttt aat gtt tat gct tta aaa gca aca tca gag ctg gat      976
Thr Ile Pro Phe Asn Val Tyr Ala Leu Lys Ala Thr Ser Glu Leu Asp
200             205                 210                 215 cta gaa atg gaa gct ctt aaa acc gtg tat aag tca ggg gaa acg att     1024
Leu Glu Met Glu Ala Leu Lys Thr Val Tyr Lys Ser Gly Glu Thr Ile
                220                 225                 230 gtg gtc acc tgt gct gtt ttt aac aat gag gtg gtt gac ctt caa tgg     1072
Val Val Thr Cys Ala Val Phe Asn Asn Glu Val Val Asp Leu Gln Trp
            235                 240                 245 act tac cct gga gaa gtg aaa ggc aaa ggc atc aca atg ctg gaa gaa     1120
Thr Tyr Pro Gly Glu Val Lys Gly Lys Gly Ile Thr Met Leu Glu Glu
            250                 255                 260 atc aaa gtc cca tcc atc aaa ttg gtg tac act ttg acg gtc ccc gag     1168
Ile Lys Val Pro Ser Ile Lys Leu Val Tyr Thr Leu Thr Val Pro Glu
265                 270                 275 gcc acg gtg aaa gac agt gga gat tac gaa tgt gct gcc cgc cag gct     1216
Ala Thr Val Lys Asp Ser Gly Asp Tyr Glu Cys Ala Ala Arg Gln Ala
280                 285                 290                 295 acc agg gag gtc aaa gaa atg aag aaa gtc act att tct gtc cat gag     1264
Thr Arg Glu Val Lys Glu Met Lys Lys Val Thr Ile Ser Val His Glu
                300                 305                 310 aaa ggt ttc att gaa atc aaa ccc acc ttc agc cag ttg gaa gct gtc     1312
Lys Gly Phe Ile Glu Ile Lys Pro Thr Phe Ser Gln Leu Glu Ala Val
            315                 320                 325 aac ctg cat gaa gtc aaa cat ttt gtt gta gag gtg cgg gcc tac cca     1360
Asn Leu His Glu Val Lys His Phe Val Val Glu Val Arg Ala Tyr Pro
            330                 335                 340 cct ccc agg ata tcc tgg ctg aaa aac aat ctg act ctg att gaa aat     1408
Pro Pro Arg Ile Ser Trp Leu Lys Asn Asn Leu Thr Leu Ile Glu Asn
345                 350                 355 ctc act gag atc acc act gat gtg gaa aag att cag gaa ata agg tat     1456
Leu Thr Glu Ile Thr Thr Asp Val Glu Lys Ile Gln Glu Ile Arg Tyr
360                 365                 370                 375 cga agc aaa tta aag ctg atc cgt gct aag gaa gaa gac agt ggc cat     1504
Arg Ser Lys Leu Lys Leu Ile Arg Ala Lys Glu Glu Asp Ser Gly His
            380                 385                 390 tat act att gta gct caa aat gaa gat gct gtg aag agc tat act ttt     1552
Tyr Thr Ile Val Ala Gln Asn Glu Asp Ala Val Lys Ser Tyr Thr Phe
            395                 400                 405 gaa ctg tta act caa gtt cct tca tcc att ctg gac ttg gtc gat gat     1600
Glu Leu Leu Thr Gln Val Pro Ser Ser Ile Leu Asp Leu Val Asp Asp
            410                 415                 420 cac cat ggc tca act ggg gga cag acg gtg agg tgc aca gct gaa ggc     1648
His His Gly Ser Thr Gly Gly Gln Thr Val Arg Cys Thr Ala Glu Gly
425                 430                 435
```

```
acg ccg ctt cct gat att gag tgg atg ata tgc aaa gat att aag aaa      1696
Thr Pro Leu Pro Asp Ile Glu Trp Met Ile Cys Lys Asp Ile Lys Lys
440                 445                 450                 455 tgt aat aat gaa act tcc tgg act att ttg gcc aac aat gtc tca aac      1744
Cys Asn Asn Glu Thr Ser Trp Thr Ile Leu Ala Asn Asn Val Ser Asn
                460                 465                 470 atc atc acg gag atc cac tcc cga gac agg agt acc gtg gag ggc cgt      1792
Ile Ile Thr Glu Ile His Ser Arg Asp Arg Ser Thr Val Glu Gly Arg
        475                 480                 485 gtg act ttc gcc aaa gtg gag gag acc atc gcc gtg cga tgc ctg gct      1840
Val Thr Phe Ala Lys Val Glu Glu Thr Ile Ala Val Arg Cys Leu Ala
            490                 495                 500 aag aat ctc ctt gga gct gag aac cga gag ctg aag ctg gtg gct ccc      1888
Lys Asn Leu Leu Gly Ala Glu Asn Arg Glu Leu Lys Leu Val Ala Pro
        505                 510                 515 acc ctg cgt tct gaa ctc acg gtg gct gct gca gtc ctg gtg ctg ttg      1936
Thr Leu Arg Ser Glu Leu Thr Val Ala Ala Ala Val Leu Val Leu Leu
520                 525                 530                 535 gtg att gtg atc atc tca ctt att gtc ctg gtt gtc att tgg aaa cag      1984
Val Ile Val Ile Ile Ser Leu Ile Val Leu Val Val Ile Trp Lys Gln
                540                 545                 550 aaa ccg agg tat gaa att cgc tgg agg gtc att gaa tca atc agc cca      2032
Lys Pro Arg Tyr Glu Ile Arg Trp Arg Val Ile Glu Ser Ile Ser Pro
                555                 560                 565 gat gga cat gaa tat att tat gtg gac ccg atg cag ctg cct tat gac      2080
Asp Gly His Glu Tyr Ile Tyr Val Asp Pro Met Gln Leu Pro Tyr Asp
        570                 575                 580 tca aga tgg gag ttt cca aga gat gga cta gtg ctt ggt cgg gtc ttg      2128
Ser Arg Trp Glu Phe Pro Arg Asp Gly Leu Val Leu Gly Arg Val Leu
585                 590                 595 ggg tct gga gcg ttt ggg aag gtg gtt gaa gga aca gcc tat gga tta      2176
Gly Ser Gly Ala Phe Gly Lys Val Val Glu Gly Thr Ala Tyr Gly Leu
                600                 605                 610                 615 agc cgg tcc caa cct gtc atg aaa gtt gca gtg aag atg cta aaa ccc      2224
Ser Arg Ser Gln Pro Val Met Lys Val Ala Val Lys Met Leu Lys Pro
                620                 625                 630 acg gcc aga tcc agt gaa aaa caa gct ctc atg tct gaa ctg aag ata      2272
Thr Ala Arg Ser Ser Glu Lys Gln Ala Leu Met Ser Glu Leu Lys Ile
                635                 640                 645 atg act cac ctg ggg cca cat ttg aac att gta aac ttg ctg gga gcc      2320
Met Thr His Leu Gly Pro His Leu Asn Ile Val Asn Leu Leu Gly Ala
            650                 655                 660 tgc acc aag tca ggc ccc att tac atc atc aca gag tat tgc ttc tat      2368
Cys Thr Lys Ser Gly Pro Ile Tyr Ile Ile Thr Glu Tyr Cys Phe Tyr
665                 670                 675 gga gat ttg gtc aac tat ttg cat aag aat agg gat agc ttc ctg agc      2416
Gly Asp Leu Val Asn Tyr Leu His Lys Asn Arg Asp Ser Phe Leu Ser
680                 685                 690                 695 cac cac cca gag aag cca aag aaa gag ctg gat atc ttt gga ttg aac      2464
His His Pro Glu Lys Pro Lys Lys Glu Leu Asp Ile Phe Gly Leu Asn
                700                 705                 710 cct gct gat gaa agc aca cgg agc tat gtt att tta tct ttt gaa aac      2512
Pro Ala Asp Glu Ser Thr Arg Ser Tyr Val Ile Leu Ser Phe Glu Asn
                715                 720                 725 aat ggt gac tac atg gac atg aag cag gct gat act aca cag tat gtc      2560
Asn Gly Asp Tyr Met Asp Met Lys Gln Ala Asp Thr Thr Gln Tyr Val
            730                 735                 740 ccc atg cta gaa agg aaa gag gtt tct aaa tat tcc gac atc cag aga      2608
Pro Met Leu Glu Arg Lys Glu Val Ser Lys Tyr Ser Asp Ile Gln Arg
        745                 750                 755
```

-continued

| | |
|---|---|
| tca ctc tat gat cgt cca gcc tca tat aag aag aaa tct atg tta gac<br>Ser Leu Tyr Asp Arg Pro Ala Ser Tyr Lys Lys Lys Ser Met Leu Asp<br>760                           765                     770                   775 | 2656 |
| tca gaa gtc aaa aac ctc ctt tca gat gat aac tca gaa ggc ctt act<br>Ser Glu Val Lys Asn Leu Leu Ser Asp Asp Asn Ser Glu Gly Leu Thr<br>                      780                     785                           790 | 2704 |
| tta ttg gat ttg ttg agc ttc acc tat caa gtt gcc cga gga atg gag<br>Leu Leu Asp Leu Leu Ser Phe Thr Tyr Gln Val Ala Arg Gly Met Glu<br>            795                         800                     805 | 2752 |
| ttt ttg gct tca aaa aat tgt gtc cac cgt gat ctg gct gct cgc aac<br>Phe Leu Ala Ser Lys Asn Cys Val His Arg Asp Leu Ala Ala Arg Asn<br>810                           815                     820 | 2800 |
| gtc ctc ctg gca caa gga aaa att gtg aag atc tgt gac ttt ggc ctg<br>Val Leu Leu Ala Gln Gly Lys Ile Val Lys Ile Cys Asp Phe Gly Leu<br>            825                         830                     835 | 2848 |
| gcc aga gac atc atg cat gat tcg aac tat gtg tcg aaa ggc agt acc<br>Ala Arg Asp Ile Met His Asp Ser Asn Tyr Val Ser Lys Gly Ser Thr<br>840                           845                     850                     855 | 2896 |
| ttt ctg ccc gtg aag tgg atg gct cct gag agc atc ttt gac aac ctc<br>Phe Leu Pro Val Lys Trp Met Ala Pro Glu Ser Ile Phe Asp Asn Leu<br>                        860                     865                     870 | 2944 |
| tac acc aca ctg agt gat gtc tgg tct tat ggc att ctg ctc tgg gag<br>Tyr Thr Thr Leu Ser Asp Val Trp Ser Tyr Gly Ile Leu Leu Trp Glu<br>              875                         880                     885 | 2992 |
| atc ttt tcc ctt ggt ggc acc cct tac ccc ggc atg atg gtg gat tct<br>Ile Phe Ser Leu Gly Gly Thr Pro Tyr Pro Gly Met Met Val Asp Ser<br>                      890                     895                          900 | 3040 |
| act ttc tac aat aag atc aag agt ggg tac cgg atg gcc aag cct gac<br>Thr Phe Tyr Asn Lys Ile Lys Ser Gly Tyr Arg Met Ala Lys Pro Asp<br>905                           910                     915 | 3088 |
| cac gct acc agt gaa gtc tac gag atc atg gtg aaa tgc tgg aac agt<br>His Ala Thr Ser Glu Val Tyr Glu Ile Met Val Lys Cys Trp Asn Ser<br>920                           925                     930                     935 | 3136 |
| gag ccg gag aag aga ccc tcc ttt tac cac ctg agt gag att gtg gag<br>Glu Pro Glu Lys Arg Pro Ser Phe Tyr His Leu Ser Glu Ile Val Glu<br>                      940                     945                     950 | 3184 |
| aat ctg ctg cct gga caa tat aaa aag agt tat gaa aaa att cac ctg<br>Asn Leu Leu Pro Gly Gln Tyr Lys Lys Ser Tyr Glu Lys Ile His Leu<br>955                           960                     965 | 3232 |
| gac ttc ctg aag agt gac cat cct gct gtg gca cgc atg cgt gtg gac<br>Asp Phe Leu Lys Ser Asp His Pro Ala Val Ala Arg Met Arg Val Asp<br>            970                         975                     980 | 3280 |
| tca gac aat gca tac att ggt gtc acc tac aaa aac gag gaa gac aag<br>Ser Asp Asn Ala Tyr Ile Gly Val Thr Tyr Lys Asn Glu Glu Asp Lys<br>985                           990                     995 | 3328 |
| ctg  aag gac tgg gag ggt  ggt ctg gat gag cag  aga ctg agc gct<br>Leu Lys Asp Trp Glu Gly Gly Leu Asp Glu Gln Arg Leu Ser Ala<br>1000                        1005                   1010 | 3373 |
| gac  agt ggc tac atc att  cct ctg cct gac att  gac cct gtc cct<br>Asp Ser Gly Tyr Ile Ile Pro Leu Pro Asp Ile Asp Pro Val Pro<br>1015                        1020                   1025 | 3418 |
| gag gag gag gac ctg ggc  aag agg aac aga cac  agc tcg cag acc<br>Glu Glu Glu Asp Leu Gly Lys Arg Asn Arg His Ser Ser Gln Thr<br>1030                        1035                   1040 | 3463 |
| tct  gaa gag agt gcc att  gag acg ggt tcc agc  agt tcc acc ttc<br>Ser Glu Glu Ser Ala Ile Glu Thr Gly Ser Ser Ser Ser Thr Phe<br>1045                        1050                   1055 | 3508 |
| atc  aag aga gag gac gag  acc att gaa gac atc  gac atg atg gat<br>Ile Lys Arg Glu Asp Glu Thr Ile Glu Asp Ile Asp Met Met Asp | 3553 |

|  |  |  |  |  |  |  |  |  |  |  |
|---|---|---|---|---|---|---|---|---|---|---|
| 1060 | | | | 1065 | | | | 1070 | | |
| gac | atc | ggc | ata | gac | tct | tca | gac | ctg | gtg | gaa | gac | agc | ttc | ctg | 3598
| Asp | Ile | Gly | Ile | Asp | Ser | Ser | Asp | Leu | Val | Glu | Asp | Ser | Phe | Leu |
| 1075 | | | | 1080 | | | | 1085 | | |

```
taa ctggcggatt cgaggggttc cttccacttc tggggccacc tctggatccc     3651
gttcagaaaa ccactttatt gcaatgcaga ggttgagagg aggacttggt tgatgtttaa  3711
agagaagttc ccagccaagg gcctcgggga gcgttctaaa tatgaatgaa tgggatattt  3771
tgaaatgaac tttgtcagtg ttgcctcttg caatgcctca gtagcatctc agtggtgtgt  3831
gaagtttgga gatagatgga taagggaata ataggccaca gaaggtgaac tttgtgcttc  3891
aaggacattg gtgagagtcc aacagacaca atttatactg cgacagaact tcagcattgt  3951
aattatgtaa ataactctaa ccaaggctgt gtttagattg tattaactat cttctttgga  4011
cttctgaaga gaccactcaa tccatccatg tacttccctc ttgaaacctg atgtcagctg  4071
ctgttgaact ttttaaagaa gtgcatgaaa accatttttt gaaccttaaa aggtactggt  4131
actatagcat tttgctatct tttttagtgt taaagagata aagaataata attaaccaac  4191
cttgtttaat agatttgggt catttagaag cctgacaact cattttcata ttgtaatcta  4251
tgtttataat actactactg ttatcagtaa tgctaaatgt gtaataatgt aacatgattt  4311
ccctccagag aaagcacaat ttaaaacaat ccttactaag taggtgatga gtttgacagt  4371
ttttgacatt tatattaaat aacatgtttc tctataaagt atggtaatag ctttagtgaa  4431
ttaaatttag ttgagcatag agaacaaagt aaaagtagtg ttgtccagga agtcagaatt  4491
tttaactgta ctgaataggt tccccaatcc atcgtattaa aaaacaatta actgccctct  4551
gaaataatgg gattagaaac aaacaaaact cttaagtcct aaaagttctc aatgtagagg  4611
cataaacctg tgctgaacat aacttctcat gtatattacc caatggaaaa tataatgatc  4671
agcaaaaaga ctggatttgc agaagttttt ttttttttt tcttcatgcc tgatgaaagc  4731
tttggcgacc ccaatatatg tatttttga atctatgaac ctgaaaaggg tcagaaggat  4791
gcccagacat cagcctcctt cttcacccc ttaccccaaa gagaaagagt ttgaaactcg  4851
agaccataaa gatattcttt agtggaggct ggatgtgcat tagcctggat cctcagttct  4911
caaatgtgtg tggcagccag gatgactaga tcctgggttt ccatccttga gattctgaag  4971
tatgaagtct gagggaaacc agagtctgta ttttctaaa ctccctggct gttctgatcg  5031
gccagttttc ggaaacactg acttaggttt caggaagttg ccatgggaaa caaataattt  5091
gaactttgga acagggttgg cattcaacca cgcaggaagc ctactattta aatccttggc  5151
ttcaggttag tgacatttaa tgccatctag ctagcaattg cgaccttaat ttaactttcc  5211
agtcttagct gaggctgaga agctaaagt tggttttga caggttttcc aaaagtaaag  5271
atgctacttc ccactgtatg ggggagattg aactttcccc gtctcccgtc ttctgcctcc  5331
cactccatac cccgccaagg aaaggcatgt acaaaaatta tgcaattcag tgttccaagt  5391
ctctgtgtaa ccagctcagt gttttggtgg aaaaaacatt ttaagttta ctgataattt  5451 gaggttagat gggaggatga attgtcacat ctatccacac tgtcaaacag gttggtgtgg  5511
gttcattggc attctttgca atactgctta attgctgata ccatatgaat gaaacatggg  5571
ctgtgattac tgcaatcact gtgctatcgg cagatgatgc tttggaagat gcagaagcaa  5631
taataaagta cttgactacc tactggtgta atctcaatgc aagccccaac tttcttatcc  5691 aacttttca tagtaagtgc gaagactgag ccagattggc caattaaaaa cgaaaacctg  5751
actaggttct gtagagccaa ttagacttga aatacgtttg tgtttctaga atcacagctc  5811
```

-continued

```
aagcattctg tttatcgctc actctcccct gtacagcctt attttgttgg tgctttgcat    5871
tttgatattg ctgtgagcct tgcatgacat catgaggccg gatgaaactt ctcagtccag    5931
cagtttccag tcctaacaaa tgctcccacc tgaatttgta tatgactgca tttgtgtgtg    5991
tgtgtgtgtt ttcagcaaat tccagatttg tttccttttg gcctcctgca aagtctccag    6051
aagaaaattt gccaatcttt cctactttct atttttatga tgacaatcaa agccggcctg    6111
agaaacacta tttgtgactt tttaaacgat tagtgatgtc cttaaaatgt ggtctgccaa    6171
tctgtacaaa atggtcctat ttttgtgaag agggacataa gataaaatga tgttatacat    6231
caatatgtat atatgtattt ctatatagac ttggagaata ctgccaaaac atttatgaca    6291
agctgtatca ctgccttcgt ttatattttt ttaactgtga taatccccac aggcacatta    6351
actgttgcac ttttgaatgt ccaaaattta tattttagaa ataataaaaa gaaagatact    6411
tacatgttcc caaaacaatg gtgtggtgaa tgtgtgagaa aaactaactt gatagggtct    6471
accaatacaa aatgtattac gaatgcccct gttcatgttt ttgttttaaa acgtgtaaat    6531
gaagatcttt atatttcaat aaatgatata taatttaaag tta                      6574
```

<210> SEQ ID NO 8
<211> LENGTH: 1089
<212> TYPE: PRT
<213> ORGANISM: Homo sapiens

<400> SEQUENCE: 8

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240
```

Glu Val Val Asp Leu Gln Trp Thr Tyr Pro Gly Val Lys Gly Lys
            245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
            290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
            370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
        740                 745                 750

Lys Tyr Ser Asp Ile Gln Arg Ser Leu Tyr Asp Arg Pro Ala Ser Tyr
    755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
        820                 825                 830

Lys Ile Cys Asp Phe Gly Leu Ala Arg Asp Ile Met His Asp Ser Asn
    835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
        900                 905                 910

Tyr Arg Met Ala Lys Pro Asp His Ala Thr Ser Glu Val Tyr Glu Ile
    915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
        980                 985                 990

Tyr Lys Asn Glu Glu Asp Lys Leu Lys Asp Trp Glu Gly Gly Leu Asp
    995                 1000                1005

Glu Gln Arg Leu Ser Ala Asp Ser Gly Tyr Ile Ile Pro Leu Pro
    1010                1015                1020

Asp Ile Asp Pro Val Pro Glu Glu Glu Asp Leu Gly Lys Arg Asn
    1025                1030                1035

Arg His Ser Ser Gln Thr Ser Glu Glu Ser Ala Ile Glu Thr Gly
    1040                1045                1050

Ser Ser Ser Ser Thr Phe Ile Lys Arg Glu Asp Glu Thr Ile Glu
    1055                1060                1065

Asp Ile Asp Met Met Asp Asp Ile Gly Ile Asp Ser Ser Asp Leu

```
                    1070              1075              1080
Val Glu  Asp Ser Phe Leu
    1085

<210> SEQ ID NO 9
<211> LENGTH: 5718
<212> TYPE: DNA
<213> ORGANISM: Homo sapiens
<220> FEATURE:
<221> NAME/KEY: CDS
<222> LOCATION: (470)..(3790)
<300> PUBLICATION INFORMATION:
<308> DATABASE ACCESSION NUMBER: NM_002609.3
<309> DATABASE ENTRY DATE: 2015-03-15
<313> RELEVANT RESIDUES IN SEQ ID NO: (1)..(5718)

<400> SEQUENCE: 9
ctcctgaggc tgccagcagc cagcagtgac tgcccgccct atctgggacc caggatcgct      60
ctgtgagcaa cttggagcca gagaggagat caacaaggag gaggagagag ccggcccctc     120
agccctgctg cccagcagca gcctgtgctc gccctgccca acgcagacag ccagacccag     180
ggcggcccct ctgcggctc tgctcctccc gaaggatgct ggggagtga ggcgaagctg     240 ggccgctcct ctcccctaca gcagccccct tcctccatcc ctctgttctc ctgagccttc     300
aggagcctgc accagtcctg cctgtccttc tactcagctg ttacccactc tgggaccagc     360
agtctttctg ataactggga gagggcagta aggaggactt cctggagggg gtgactgtcc     420
agagcctgga actgtgccca caccagaagc catcagcagc aaggacacc atg cgg ctt      478
                                                   Met Arg Leu
                                                     1 ccg ggt gcg atg cca gct ctg gcc ctc aaa ggc gag ctg ctg ttg ctg       526
Pro Gly Ala Met Pro Ala Leu Ala Leu Lys Gly Glu Leu Leu Leu Leu
      5                  10                  15 tct ctc ctg tta ctt ctg gaa cca cag atc tct cag ggc ctg gtc gtc       574
Ser Leu Leu Leu Leu Leu Glu Pro Gln Ile Ser Gln Gly Leu Val Val
 20                  25                  30                  35 aca ccc ccg ggg cca gag ctt gtc ctc aat gtc tcc agc acc ttc gtt       622
Thr Pro Pro Gly Pro Glu Leu Val Leu Asn Val Ser Ser Thr Phe Val
              40                  45                  50 ctg acc tgc tcg ggt tca gct ccg gtg gtg tgg gaa cgg atg tcc cag       670
Leu Thr Cys Ser Gly Ser Ala Pro Val Val Trp Glu Arg Met Ser Gln
          55                  60                  65 gag ccc cca cag gaa atg gcc aag gcc cag gat ggc acc ttc tcc agc       718
Glu Pro Pro Gln Glu Met Ala Lys Ala Gln Asp Gly Thr Phe Ser Ser
      70                  75                  80 gtg ctc aca ctg acc aac ctc act ggg cta gac acg gga gaa tac ttt       766
Val Leu Thr Leu Thr Asn Leu Thr Gly Leu Asp Thr Gly Glu Tyr Phe
 85                  90                  95 tgc acc cac aat gac tcc cgt gga ctg gag acc gat gag cgg aaa cgg       814
Cys Thr His Asn Asp Ser Arg Gly Leu Glu Thr Asp Glu Arg Lys Arg
100                 105                 110                 115 ctc tac atc ttt gtg cca gat ccc acc gtg ggc ttc ctc cct aat gat       862
Leu Tyr Ile Phe Val Pro Asp Pro Thr Val Gly Phe Leu Pro Asn Asp
              120                 125                 130 gcc gag gaa cta ttc atc ttt ctc acg gaa ata act gag atc acc att       910
Ala Glu Glu Leu Phe Ile Phe Leu Thr Glu Ile Thr Glu Ile Thr Ile
          135                 140                 145 cca tgc cga gta aca gac cca cag ctg gtg gtg aca ctg cac gag aag       958
Pro Cys Arg Val Thr Asp Pro Gln Leu Val Val Thr Leu His Glu Lys
      150                 155                 160 aaa ggg gac gtt gca ctg cct gtc ccc tat gat cac caa cgt ggc ttt      1006
```

|   |   |   |   |   |   |   |   |   |   |   |   |   |   |
|---|---|---|---|---|---|---|---|---|---|---|---|---|---|
| Lys | Gly | Asp | Val | Ala | Leu | Pro | Val | Pro | Tyr | Asp | His | Gln | Arg | Gly | Phe |
| 165 | | | | 170 | | | | | 175 | | | | |

```
tct ggt atc ttt gag gac aga agc tac atc tgc aaa acc acc att ggg    1054
Ser Gly Ile Phe Glu Asp Arg Ser Tyr Ile Cys Lys Thr Thr Ile Gly
180             185                 190                 195 gac agg gag gtg gat tct gat gcc tac tat gtc tac aga ctc cag gtg    1102
Asp Arg Glu Val Asp Ser Asp Ala Tyr Tyr Val Tyr Arg Leu Gln Val
                200                 205                 210 tca tcc atc aac gtc tct gtg aac gca gtg cag act gtg gtc cgc cag    1150
Ser Ser Ile Asn Val Ser Val Asn Ala Val Gln Thr Val Val Arg Gln
            215                 220                 225 ggt gag aac atc acc ctc atg tgc att gtg atc ggg aat gag gtg gtc    1198
Gly Glu Asn Ile Thr Leu Met Cys Ile Val Ile Gly Asn Glu Val Val
        230                 235                 240 aac ttc gag tgg aca tac ccc gcc aaa gaa agt ggg cgg ctg gtg gag    1246
Asn Phe Glu Trp Thr Tyr Pro Arg Lys Glu Ser Gly Arg Leu Val Glu
    245                 250                 255 ccg gtg act gac ttc ctc ttg gat atg cct tac cac atc cgc tcc atc    1294
Pro Val Thr Asp Phe Leu Leu Asp Met Pro Tyr His Ile Arg Ser Ile
260                 265                 270                 275 ctg cac atc ccc agt gcc gag tta gaa gac tcg ggg acc tac acc tgc    1342
Leu His Ile Pro Ser Ala Glu Leu Glu Asp Ser Gly Thr Tyr Thr Cys
                280                 285                 290 aat gtg acg gag agt gtg aat gac cat cag gat gaa aag gcc atc aac    1390
Asn Val Thr Glu Ser Val Asn Asp His Gln Asp Glu Lys Ala Ile Asn
            295                 300                 305 atc acc gtg gtt gag agc ggc tac gtg cgg ctc ctg gga gag gtg ggc    1438
Ile Thr Val Val Glu Ser Gly Tyr Val Arg Leu Leu Gly Glu Val Gly
        310                 315                 320 aca cta caa ttt gct gag ctg cat cgg agc cgg aca ctg cag gta gtg    1486
Thr Leu Gln Phe Ala Glu Leu His Arg Ser Arg Thr Leu Gln Val Val
    325                 330                 335 ttc gag gcc tac cca ccg ccc act gtc ctg tgg ttc aaa gac aac cgc    1534
Phe Glu Ala Tyr Pro Pro Pro Thr Val Leu Trp Phe Lys Asp Asn Arg
340                 345                 350                 355 acc ctg ggc gac tcc agc gct ggc gaa atc gcc ctg tcc acg cgc aac    1582
Thr Leu Gly Asp Ser Ser Ala Gly Glu Ile Ala Leu Ser Thr Arg Asn
                360                 365                 370 gtg tcg gag acc cgg tat gtg tca gag ctg aca ctg gtt cgc gtg aag    1630
Val Ser Glu Thr Arg Tyr Val Ser Glu Leu Thr Leu Val Arg Val Lys
            375                 380                 385 gtg gca gag gct ggc cac tac acc atg cgg gcc ttc cat gag gat gct    1678
Val Ala Glu Ala Gly His Tyr Thr Met Arg Ala Phe His Glu Asp Ala
        390                 395                 400 gag gtc cag ctc tcc ttc cag cta cag atc aat gtc cct gtc cga gtg    1726
Glu Val Gln Leu Ser Phe Gln Leu Gln Ile Asn Val Pro Val Arg Val
    405                 410                 415 ctg gag cta agt gag agc cac cct gac agt ggg gaa cag aca gtc cgc    1774
Leu Glu Leu Ser Glu Ser His Pro Asp Ser Gly Glu Gln Thr Val Arg
420                 425                 430                 435 tgt cgt ggc cgg ggc atg ccc cag ccg aac atc atc tgg tct gcc tgc    1822
Cys Arg Gly Arg Gly Met Pro Gln Pro Asn Ile Ile Trp Ser Ala Cys
                440                 445                 450 aga gac ctc aaa agg tgt cca cgt gag ctg ccg ccc acg ctg ctg ggg    1870
Arg Asp Leu Lys Arg Cys Pro Arg Glu Leu Pro Pro Thr Leu Leu Gly
            455                 460                 465 aac agt tcc gaa gag gag agc cag ctg gag act aac gtg acg tac tgg    1918
Asn Ser Ser Glu Glu Glu Ser Gln Leu Glu Thr Asn Val Thr Tyr Trp
        470                 475                 480
```

| | | |
|---|---|---|
| gag gag gag cag gag ttt gag gtg gtg agc aca ctg cgt ctg cag cac<br>Glu Glu Glu Gln Glu Phe Glu Val Val Ser Thr Leu Arg Leu Gln His<br>485      490           495 | 1966 | |
| gtg gat cgg cca ctg tcg gtg cgc tgc acg ctg cgc aac gct gtg ggc<br>Val Asp Arg Pro Leu Ser Val Arg Cys Thr Leu Arg Asn Ala Val Gly<br>500           505              510           515 | 2014 | |
| cag gac acg cag gag gtc atc gtg gtg cca cac tcc ttg ccc ttt aag<br>Gln Asp Thr Gln Glu Val Ile Val Val Pro His Ser Leu Pro Phe Lys<br>              520           525           530 | 2062 | |
| gtg gtg gtg atc tca gcc atc ctg gcc ctg gtg gtg ctc acc atc atc<br>Val Val Val Ile Ser Ala Ile Leu Ala Leu Val Val Leu Thr Ile Ile<br>535           540           545 | 2110 | |
| tcc ctt atc atc ctc atc atg ctt tgg cag aag aag cca cgt tac gag<br>Ser Leu Ile Ile Leu Ile Met Leu Trp Gln Lys Lys Pro Arg Tyr Glu<br>      550           555           560 | 2158 | |
| atc cga tgg aag gtg att gag tct gtg agc tct gac ggc cat gag tac<br>Ile Arg Trp Lys Val Ile Glu Ser Val Ser Ser Asp Gly His Glu Tyr<br>565           570           575 | 2206 | |
| atc tac gtg gac ccc atg cag ctg ccc tat gac tcc acg tgg gag ctg<br>Ile Tyr Val Asp Pro Met Gln Leu Pro Tyr Asp Ser Thr Trp Glu Leu<br>580           585           590           595 | 2254 | |
| ccg cgg gac cag ctt gtg ctg gga cgc acc ctc ggc tct ggg gcc ttt<br>Pro Arg Asp Gln Leu Val Leu Gly Arg Thr Leu Gly Ser Gly Ala Phe<br>              600           605           610 | 2302 | |
| ggg cag gtg gtg gag gcc acg gct cat ggc ctg agc cat tct cag gcc<br>Gly Gln Val Val Glu Ala Thr Ala His Gly Leu Ser His Ser Gln Ala<br>      615           620           625 | 2350 | |
| acg atg aaa gtg gcc gtc aag atg ctt aaa tcc aca gcc cgc agc agt<br>Thr Met Lys Val Ala Val Lys Met Leu Lys Ser Thr Ala Arg Ser Ser<br>630           635           640 | 2398 | |
| gag aag caa gcc ctt atg tcg gag ctg aag atc atg agt cac ctt ggg<br>Glu Lys Gln Ala Leu Met Ser Glu Leu Lys Ile Met Ser His Leu Gly<br>645           650           655 | 2446 | |
| ccc cac ctg aac gtg gtc aac ctg ttg ggg gcc tgc acc aaa gga gga<br>Pro His Leu Asn Val Val Asn Leu Leu Gly Ala Cys Thr Lys Gly Gly<br>660           665           670           675 | 2494 | |
| ccc atc tat atc atc act gag tac tgc cgc tac gga gac ctg gtg gac<br>Pro Ile Tyr Ile Ile Thr Glu Tyr Cys Arg Tyr Gly Asp Leu Val Asp<br>              680           685           690 | 2542 | |
| tac ctg cac cgc aac aaa cac acc ttc ctg cag cac cac tcc gac aag<br>Tyr Leu His Arg Asn Lys His Thr Phe Leu Gln His His Ser Asp Lys<br>      695           700           705 | 2590 | |
| cgc cgc ccg ccc agc gcg gag ctc tac agc aat gct ctg ccc gtt ggg<br>Arg Arg Pro Pro Ser Ala Glu Leu Tyr Ser Asn Ala Leu Pro Val Gly<br>710           715           720 | 2638 | |
| ctc ccc ctg ccc agc cat gtg tcc ttg acc ggg gag agc gac ggt ggc<br>Leu Pro Leu Pro Ser His Val Ser Leu Thr Gly Glu Ser Asp Gly Gly<br>725           730           735 | 2686 | |
| tac atg gac atg agc aag gac gag tcg gtg gac tat gtg ccc atg ctg<br>Tyr Met Asp Met Ser Lys Asp Glu Ser Val Asp Tyr Val Pro Met Leu<br>740           745           750           755 | 2734 | |
| gac atg aaa gga gac gtc aaa tat gca gac atc gag tcc tcc aac tac<br>Asp Met Lys Gly Asp Val Lys Tyr Ala Asp Ile Glu Ser Ser Asn Tyr<br>              760           765           770 | 2782 | |
| atg gcc cct tac gat aac tac gtt ccc tct gcc cct gag agg acc tgc<br>Met Ala Pro Tyr Asp Asn Tyr Val Pro Ser Ala Pro Glu Arg Thr Cys<br>      775           780           785 | 2830 | |
| cga gca act ttg atc aac gag tct cca gtg cta agc tac atg gac ctc<br>Arg Ala Thr Leu Ile Asn Glu Ser Pro Val Leu Ser Tyr Met Asp Leu<br>790           795           800 | 2878 | |

```
gtg ggc ttc agc tac cag gtg gcc aat ggc atg gag ttt ctg gcc tcc    2926
Val Gly Phe Ser Tyr Gln Val Ala Asn Gly Met Glu Phe Leu Ala Ser
805                 810                 815 aag aac tgc gtc cac aga gac ctg gcg gct agg aac gtg ctc atc tgt    2974
Lys Asn Cys Val His Arg Asp Leu Ala Ala Arg Asn Val Leu Ile Cys
820                 825                 830                 835 gaa ggc aag ctg gtc aag atc tgt gac ttt ggc ctg gct cga gac atc    3022
Glu Gly Lys Leu Val Lys Ile Cys Asp Phe Gly Leu Ala Arg Asp Ile
                840                 845                 850 atg cgg gac tcg aat tac atc tcc aaa ggc agc acc ttt ttg cct tta    3070
Met Arg Asp Ser Asn Tyr Ile Ser Lys Gly Ser Thr Phe Leu Pro Leu
            855                 860                 865 aag tgg atg gct ccg gag agc atc ttc aac agc ctc tac acc acc ctg    3118
Lys Trp Met Ala Pro Glu Ser Ile Phe Asn Ser Leu Tyr Thr Thr Leu
        870                 875                 880 agc gac gtg tgg tcc ttc ggg atc ctg ctc tgg gag atc ttc acc ttg    3166
Ser Asp Val Trp Ser Phe Gly Ile Leu Leu Trp Glu Ile Phe Thr Leu
    885                 890                 895 ggt ggc acc cct tac cca gag ctg ccc atg aac gag cag ttc tac aat    3214
Gly Gly Thr Pro Tyr Pro Glu Leu Pro Met Asn Glu Gln Phe Tyr Asn
900                 905                 910                 915 gcc atc aaa cgg ggt tac cgc atg gcc cag cct gcc cat gcc tcc gac    3262
Ala Ile Lys Arg Gly Tyr Arg Met Ala Gln Pro Ala His Ala Ser Asp
                920                 925                 930 gag atc tat gag atc atg cag aag tgc tgg gaa gag aag ttt gag att    3310
Glu Ile Tyr Glu Ile Met Gln Lys Cys Trp Glu Glu Lys Phe Glu Ile
            935                 940                 945 cgg ccc ccc ttc tcc cag ctg gtg ctg ctt ctc gag aga ctg ttg ggc    3358
Arg Pro Pro Phe Ser Gln Leu Val Leu Leu Leu Glu Arg Leu Leu Gly
        950                 955                 960 gaa ggt tac aaa aag aag tac cag cag gtg gat gag gag ttt ctg agg    3406
Glu Gly Tyr Lys Lys Lys Tyr Gln Gln Val Asp Glu Glu Phe Leu Arg
    965                 970                 975 agt gac cac cca gcc atc ctt cgg tcc cag gcc cgc ttg cct ggg ttc    3454
Ser Asp His Pro Ala Ile Leu Arg Ser Gln Ala Arg Leu Pro Gly Phe
980                 985                 990                 995 cat ggc ctc cga tct  ccc ctg gac acc agc  tcc gtc ctc tat act      3499
His Gly Leu Arg Ser Pro Leu Asp Thr Ser Ser Val Leu Tyr Thr
                1000                1005                1010 gcc gtg cag ccc aat  gag ggt gac aac gac  tat atc atc ccc ctg      3544
Ala Val Gln Pro Asn Glu Gly Asp Asn Asp Tyr Ile Ile Pro Leu
                1015                1020                1025 cct gac ccc aaa ccc  gag gtt gct gac gag  ggc cca ctg gag ggt      3589
Pro Asp Pro Lys Pro Glu Val Ala Asp Glu Gly Pro Leu Glu Gly
                1030                1035                1040 tcc ccc agc cta gcc  agc tcc acc ctg aat  gaa gtc aac acc tcc      3634
Ser Pro Ser Leu Ala Ser Ser Thr Leu Asn Glu Val Asn Thr Ser
                1045                1050                1055 tca acc atc tcc tgt  gac agc ccc ctg gag  ccc cag gac gaa cca      3679
Ser Thr Ile Ser Cys Asp Ser Pro Leu Glu Pro Gln Asp Glu Pro
                1060                1065                1070 gag cca gag ccc cag  ctt gag ctc cag gtg  gag ccg gag cca gag      3724
Glu Pro Glu Pro Gln Leu Glu Leu Gln Val Glu Pro Glu Pro Glu
                1075                1080                1085 ctg gaa cag ttg ccg  gat tcg ggg tgc cct  gcg cct cgg gcg gaa      3769
Leu Glu Gln Leu Pro Asp Ser Gly Cys Pro Ala Pro Arg Ala Glu
                1090                1095                1100 gca gag gat agc ttc  ctg tag ggggctggcc cctaccctgc cctgcctgaa      3820
Ala Glu Asp Ser Phe Leu
```

```
gctcccccc   tgccagcacc   cagcatctcc   tggcctggcc   tgaccgggct   tcctgtcagc    3880
caggctgccc   ttatcagctg   tccccttctg   gaagctttct   gctcctgacg   tgttgtgccc    3940
caaaccctgg   ggctggctta   ggaggcaaga   aaactgcagg   ggccgtgacc   agccctctgc    4000
ctccagggag   gccaactgac   tctgagccag   ggttcccca    gggaactcag   ttttcccata    4060
tgtaagatgg   gaaagttagg   cttgatgacc   cagaatctag   gattctctcc   ctggctgaca    4120
ggtggggaga   ccgaatccct   ccctgggaag   attcttggag   ttactgaggt   ggtaaattaa    4180
cttttttctg   ttcagccagc   tacccctcaa   ggaatcatag   ctctctcctc   gcactttat     4240 ccacccagga   gctagggaag   agaccctagc   ctccctggct   gctggctgag   ctagggccta    4300
gccttgagca   gtgttgcctc   atccagaaga   aagccagtct   cctccctatg   atgccagtcc    4360
ctgcgttccc   tggcccgagc   tggtctgggg   ccattaggca   gcctaattaa   tgctggaggc    4420
tgagccaagt   acaggacacc   cccagcctgc   agcccttgcc   cagggcactt   ggagcacacg    4480
cagccatagc   aagtgcctgt   gtccctgtcc   ttcaggccca   tcagtcctgg   ggcttttct     4540 ttatcaccct   cagtcttaat   ccatccacca   gagtctagaa   ggccagacgg   gccccgcatc    4600
tgtgatgaga   atgtaaatgt   gccagtgtgg   agtggccacg   tgtgtgtgcc   agtatatggc    4660
cctggctctg   cattggacct   gctatgaggc   tttggaggaa   tccctcaccc   tctctgggcc    4720
tcagtttccc   cttcaaaaaa   tgaataagtc   ggacttatta   actctgagtg   ccttgccagc    4780
actaacattc   tagagtattc   caggtggttg   cacatttgtc   cagatgaagc   aaggccatat    4840
accctaaact   tccatcctgg   gggtcagctg   ggctcctggg   agattccaga   tcacacatca    4900
cactctgggg   actcaggaac   catgccccctt  ccccaggccc   ccagcaagtc   tcaagaacac    4960
agctgcacag   gccttgactt   agagtgacag   ccggtgtcct   ggaaagcccc   cagcagctgc    5020
cccagggaca   tgggaagacc   acgggacctc   tttcactacc   cacgatgacc   tccggggta    5080 tcctgggcaa   aagggacaaa   gagggcaaat   gagatcacct   cctgcagccc   accactccag    5140
cacctgtgcc   gaggtctgcg   tcgaagacag   aatggacagt   gaggacagtt   atgtcttgta    5200
aaagacaaga   agcttcagat   gggtaccca   agaaggatgt   gagaggtggg   cgctttggag    5260
gtttgcccct   cacccaccag   ctgccccatc   cctgaggcag   cgctccatgg   gggtatggtt    5320
ttgtcactgc   ccagacctag   cagtgacatc   tcattgtccc   cagcccagtg   ggcattggag    5380
gtgccagggg   agtcagggtt   gtagccaaga   cgccccgca   cggggagggt   tgggaagggg    5440
gtgcaggaag   ctcaacccct   ctgggcacca   accctgcatt   gcaggttggc   accttacttc    5500
cctgggatcc   ccagagttgg   tccaaggagg   gagagtgggt   tctcaatacg   gtaccaaga    5560 tataatcacc   taggtttaca   aatatttta    ggactcacgt   taactcacat   ttatacagca    5620
gaaatgctat   tttgtatgct   gttaagtttt   tctatctgtg   tacttttttt   taagggaaag    5680
attttaatat   taaacctggt   gcttctcact   cacaaaaa                                5718
```

<210> SEQ ID NO 10
<211> LENGTH: 1106
<212> TYPE: PRT
<213> ORGANISM: Homo sapiens

<400> SEQUENCE: 10

Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
                20                  25                  30

```
Leu Val Val Thr Pro Pro Gly Pro Glu Leu Val Leu Asn Val Ser Ser
         35                  40                  45

Thr Phe Val Leu Thr Cys Ser Gly Ser Ala Pro Val Val Trp Glu Arg
 50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                 85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
            435                 440                 445
```

-continued

```
Ser Ala Cys Arg Asp Leu Lys Arg Cys Pro Arg Glu Leu Pro Pro Thr
    450                 455                 460
Leu Leu Gly Asn Ser Ser Glu Glu Ser Gln Leu Glu Thr Asn Val
465                 470                 475                 480
Thr Tyr Trp Glu Glu Glu Gln Glu Phe Glu Val Val Ser Thr Leu Arg
                    485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Pro His Ser Leu
            515                 520                 525
Pro Phe Lys Val Val Ile Ser Ala Ile Leu Ala Leu Val Val Leu
530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                    565                 570                 575
His Glu Tyr Ile Tyr Val Asp Pro Met Gln Leu Pro Tyr Asp Ser Thr
            580                 585                 590
Trp Glu Leu Pro Arg Asp Gln Leu Val Leu Gly Arg Thr Leu Gly Ser
            595                 600                 605
Gly Ala Phe Gly Gln Val Val Glu Ala Thr Ala His Gly Leu Ser His
            610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                    645                 650                 655
His Leu Gly Pro His Leu Asn Val Val Asn Leu Leu Gly Ala Cys Thr
            660                 665                 670
Lys Gly Gly Pro Ile Tyr Ile Ile Thr Glu Tyr Cys Arg Tyr Gly Asp
            675                 680                 685
Leu Val Asp Tyr Leu His Arg Asn Lys His Thr Phe Leu Gln His His
            690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
                    725                 730                 735
Asp Gly Gly Tyr Met Asp Met Ser Lys Asp Glu Ser Val Asp Tyr Val
                    740                 745                 750
Pro Met Leu Asp Met Lys Gly Asp Val Lys Tyr Ala Asp Ile Glu Ser
            755                 760                 765
Ser Asn Tyr Met Ala Pro Tyr Asp Asn Tyr Val Pro Ser Ala Pro Glu
770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                    805                 810                 815
Leu Ala Ser Lys Asn Cys Val His Arg Asp Leu Ala Ala Arg Asn Val
            820                 825                 830
Leu Ile Cys Glu Gly Lys Leu Val Lys Ile Cys Asp Phe Gly Leu Ala
            835                 840                 845
Arg Asp Ile Met Arg Asp Ser Asn Tyr Ile Ser Lys Gly Ser Thr Phe
850                 855                 860
Leu Pro Leu Lys Trp Met Ala Pro Glu Ser Ile Phe Asn Ser Leu Tyr
```

```
                865                 870                 875                 880
      Thr  Thr  Leu  Ser  Asp  Val  Trp  Ser  Phe  Gly  Ile  Leu  Leu  Trp  Glu  Ile
                          885                 890                 895

Phe  Thr  Leu  Gly  Gly  Thr  Pro  Tyr  Pro  Glu  Leu  Pro  Met  Asn  Glu  Gln
                          900                 905                 910

Phe  Tyr  Asn  Ala  Ile  Lys  Arg  Gly  Tyr  Arg  Met  Ala  Gln  Pro  Ala  His
                          915                 920                 925

Ala  Ser  Asp  Glu  Ile  Tyr  Glu  Ile  Met  Gln  Lys  Cys  Trp  Glu  Glu  Lys
                     930                 935                 940

Phe  Glu  Ile  Arg  Pro  Pro  Phe  Ser  Gln  Leu  Val  Leu  Leu  Leu  Glu  Arg
      945                 950                 955                 960

Leu  Leu  Gly  Glu  Gly  Tyr  Lys  Lys  Tyr  Gln  Gln  Val  Asp  Glu  Glu
                          965                 970                 975

Phe  Leu  Arg  Ser  Asp  His  Pro  Ala  Ile  Leu  Arg  Ser  Gln  Ala  Arg  Leu
                     980                 985                 990

Pro  Gly  Phe  His  Gly  Leu  Arg  Ser   Pro  Leu  Asp  Thr  Ser   Ser  Val  Leu
                          995                 1000                1005

Tyr  Thr   Ala  Val  Gln  Pro  Asn   Glu  Gly  Asp  Asn   Asp  Tyr  Ile  Ile
                     1010                1015                1020

Pro  Leu  Pro  Asp  Pro  Lys  Pro   Glu  Val  Ala  Asp  Glu   Gly  Pro  Leu
                     1025                1030                1035

Glu  Gly   Ser  Pro  Ser  Leu  Ala   Ser  Ser  Thr  Leu  Asn   Glu  Val  Asn
                     1040                1045                1050

Thr  Ser   Ser  Thr  Ile  Ser  Cys   Asp  Ser  Pro  Leu  Glu   Pro  Gln  Asp
                     1055                1060                1065

Glu  Pro   Glu  Pro  Glu  Pro  Gln   Leu  Glu  Leu  Gln  Val   Glu  Pro  Glu
                     1070                1075                1080

Pro  Glu   Leu  Glu  Gln  Leu  Pro   Asp  Ser  Gly  Cys  Pro   Ala  Pro  Arg
                     1085                1090                1095

Ala  Glu   Ala  Glu  Asp  Ser  Phe   Leu
                     1100                1105

<210> SEQ ID NO 11
<211> LENGTH: 3420
<212> TYPE: DNA
<213> ORGANISM: Homo sapiens
<220> FEATURE:
<221> NAME/KEY: CDS
<222> LOCATION: (126)..(1409)
<300> PUBLICATION INFORMATION:
<308> DATABASE ACCESSION NUMBER: NM_002507.3
<309> DATABASE ENTRY DATE: 2015-03-15
<313> RELEVANT RESIDUES IN SEQ ID NO: (1)..(3420)

<400> SEQUENCE: 11
agagcgagcc  gagccgcggc  cagctccggc  gggcagggg   ggcgctggag  cgcagcgcag      60
cgcagcccca  tcagtccgca  aagcggaccg  agctggaagt  cgagcgctgc  gcgggaggc     120 gggcg atg ggg gca ggt gcc acc ggc cgc gcc atg gac ggg ccg cgc ctg         170
      Met Gly Ala Gly Ala Thr Gly Arg Ala Met Asp Gly Pro Arg Leu
       1               5                  10                  15 ctg ctg ttg ctg ctt ctg ggg gtg tcc ctt gga ggt gcc aag gag gca            218
Leu Leu Leu Leu Leu Leu Gly Val Ser Leu Gly Gly Ala Lys Glu Ala
                 20                  25                  30 tgc ccc aca ggc ctg tac aca cac agc ggt gag tgc tgc aaa gcc tgc            266
Cys Pro Thr Gly Leu Tyr Thr His Ser Gly Glu Cys Cys Lys Ala Cys
             35                  40                  45 aac ctg ggc gag ggt gtg gcc cag cct tgt gga gcc aac cag acc gtg            314
```

```
            Asn Leu Gly Glu Gly Val Ala Gln Pro Cys Gly Ala Asn Gln Thr Val
                 50                  55                  60 tgt gag ccc tgc ctg gac agc gtg acg ttc tcc gac gtg gtg agc gcg          362
Cys Glu Pro Cys Leu Asp Ser Val Thr Phe Ser Asp Val Val Ser Ala
 65                  70                  75 acc gag ccg tgc aag ccg tgc acc gag tgc gtg ggg ctc cag agc atg          410
Thr Glu Pro Cys Lys Pro Cys Thr Glu Cys Val Gly Leu Gln Ser Met
 80                  85                  90                  95 tcg gcg ccg tgc gtg gag gcc gac gac gcc gtg tgc cgc tgc gcc tac          458
Ser Ala Pro Cys Val Glu Ala Asp Asp Ala Val Cys Arg Cys Ala Tyr
                    100                 105                 110 ggc tac tac cag gat gag acg act ggg cgc tgc gag gcg tgc cgc gtg          506
Gly Tyr Tyr Gln Asp Glu Thr Thr Gly Arg Cys Glu Ala Cys Arg Val
                115                 120                 125 tgc gag gcg ggc tcg ggc ctc gtg ttc tcc tgc cag gac aag cag aac          554
Cys Glu Ala Gly Ser Gly Leu Val Phe Ser Cys Gln Asp Lys Gln Asn
            130                 135                 140 acc gtg tgc gag gag tgc ccc gac ggc acg tat tcc gac gag gcc aac          602
Thr Val Cys Glu Glu Cys Pro Asp Gly Thr Tyr Ser Asp Glu Ala Asn
        145                 150                 155 cac gtg gac ccg tgc ctg ccc tgc acc gtg tgc gag gac acc gag cgc          650
His Val Asp Pro Cys Leu Pro Cys Thr Val Cys Glu Asp Thr Glu Arg
160                 165                 170                 175 cag ctc cgc gag tgc aca cgc tgg gcc gac gcc gag tgc gag gag atc          698
Gln Leu Arg Glu Cys Thr Arg Trp Ala Asp Ala Glu Cys Glu Glu Ile
                    180                 185                 190 cct ggc cgt tgg att aca cgg tcc aca ccc cca gag ggc tcg gac agc          746
Pro Gly Arg Trp Ile Thr Arg Ser Thr Pro Pro Glu Gly Ser Asp Ser
                195                 200                 205 aca gcc ccc agc acc cag gag cct gag gca cct cca gaa caa gac ctc          794
Thr Ala Pro Ser Thr Gln Glu Pro Glu Ala Pro Pro Glu Gln Asp Leu
            210                 215                 220 ata gcc agc acg gtg gca ggt gtg gtg acc aca gtg atg ggc agc tcc          842
Ile Ala Ser Thr Val Ala Gly Val Val Thr Thr Val Met Gly Ser Ser
        225                 230                 235 cag ccc gtg gtg acc cga ggc acc acc gac aac ctc atc cct gtc tat          890
Gln Pro Val Val Thr Arg Gly Thr Thr Asp Asn Leu Ile Pro Val Tyr
240                 245                 250                 255 tgc tcc atc ctg gct gct gtg gtt gtg ggc ctt gtg gcc tac ata gcc          938
Cys Ser Ile Leu Ala Ala Val Val Val Gly Leu Val Ala Tyr Ile Ala
                    260                 265                 270 ttc aag agg tgg aac agc tgc aag cag aac aag caa gga gcc aac agc          986
Phe Lys Arg Trp Asn Ser Cys Lys Gln Asn Lys Gln Gly Ala Asn Ser
                275                 280                 285 cgg cca gtg aac cag acg ccc cca gag gga gaa aaa ctc cac agc             1034
Arg Pro Val Asn Gln Thr Pro Pro Glu Gly Glu Lys Leu His Ser
            290                 295                 300 gac agt ggc atc tcc gtg gac agc cag agc ctg cat gac cag cag ccc         1082
Asp Ser Gly Ile Ser Val Asp Ser Gln Ser Leu His Asp Gln Gln Pro
        305                 310                 315 cac acg cag aca gcc tcg ggc cag gcc ctc aag ggt gac gga ggc ctc         1130
His Thr Gln Thr Ala Ser Gly Gln Ala Leu Lys Gly Asp Gly Gly Leu
320                 325                 330                 335 tac agc agc ctg ccc cca gcc aag cgg gag gag gtg gag aag ctt ctc         1178
Tyr Ser Ser Leu Pro Pro Ala Lys Arg Glu Glu Val Glu Lys Leu Leu
                    340                 345                 350 aac ggc tct gcg ggg gac acc tgg cgg cac ctg gcg ggc gag ctg ggc         1226
Asn Gly Ser Ala Gly Asp Thr Trp Arg His Leu Ala Gly Glu Leu Gly
                355                 360                 365
```

| | |
|---|---|
| tac cag ccc gag cac ata gac tcc ttt acc cat gag gcc tgc ccc gtt<br>Tyr Gln Pro Glu His Ile Asp Ser Phe Thr His Glu Ala Cys Pro Val<br>370                              375                     380 | 1274 |
| cgc gcc ctg ctt gca agc tgg gcc acc cag gac agc gcc aca ctg gac<br>Arg Ala Leu Leu Ala Ser Trp Ala Thr Gln Asp Ser Ala Thr Leu Asp<br>385                             390                        395 | 1322 |
| gcc ctc ctg gcc gcc ctg cgc cgc atc cag cga gcc gac ctc gtg gag<br>Ala Leu Leu Ala Ala Leu Arg Arg Ile Gln Arg Ala Asp Leu Val Glu<br>400                         405                    410                  415 | 1370 |
| agt ctg tgc agt gag tcc act gcc aca tcc ccg gtg tga gcccaaccgg<br>Ser Leu Cys Ser Glu Ser Thr Ala Thr Ser Pro Val<br>                  420                    425 | 1419 |
| ggagccccg ccccgccca cattccgaca accgatgctc cagccaaccc ctgtggagcc | 1479 |
| cgcaccccca cccttttgggg ggggcccgcc tggcagaact gagctcctct gggcaggacc | 1539 |
| tcagagtcca ggcccccaaaa ccacagccct gtcagtgcag cccgtgtggc cccttcactt | 1599 |
| ctgaccacac ttcctgtcca gagagagaag tgccccctgct gcctccccaa ccctgccct | 1659 |
| gccccgtcac catctcaggc cacctgcccc cttctcccac actgctaggt gggccagccc | 1719 |
| ctcccaccac agcaggtgtc atatatgggg ggccaacacc agggatggta ctagggggaa | 1779 |
| gtgacaaggc cccagagact cagagggagg aatcgaggaa ccagagccat ggactctaca | 1839 |
| ctgtgaactt ggggaacaag ggtggcatcc cagtggcctc aaccctccct cagcccctct | 1899 |
| tgcccccac cccagcctaa gatgaagagg atcgaggct tgtcagagct ggggaggggtt | 1959 |
| ttcgaagctc agcccacccc cctcatttg gatataggtc agtgaggccc agggagaggc | 2019 |
| catgattcgc ccaaagccag acagcaacgg ggaggcaag tgcaggctgg caccgccttc | 2079 |
| tctaaatgag gggcctcagg tttgcctgag ggcgagggga gggtggcagg tgaccttctg | 2139 |
| ggaaatggct tgaagccaag tcagcttttgc cttccacgct gtctccagac ccccacccct | 2199 |
| tccccactgc ctgcccaccc gtggagatgg gatgcttgcc tagggcctgg tccatgatgg | 2259 |
| agtcaggttt ggggttcgtg gaagggtgc tgcttccctc tgcctgtccc tctcaggcat | 2319 |
| gcctgtgtga catcagtggc atggctccag tctgctgccc tccatcccga catggacccg | 2379 |
| gagctaaacac tggccctag aatcagccta ggggtcaggg accaaggacc cctcaccttg | 2439 |
| caacacacag acacacgcac acacacacac aggaggagaa atctcacttt tctccatgag | 2499 |
| tttttttctct tgggctgaga ctggatactg cccggggcag ctgccagaga agcatcggag | 2559 |
| ggaattgagg tctgctcggc cgtcttcact cgcccccggg tttggcgggc caaggactgc | 2619 |
| cgaccgaggc tggagctggc gtctgtcttc aagggcttac acgtggagga atgctccccc | 2679 |
| atcctcccct tccctgcaaa catggggttg gctgggccca gaaggttgtg atgaagaaaa | 2739 |
| gtgggccagt gtgggaatgc ggcaagaagg aattgacttc gactgtgacc tgtgggatt | 2799 |
| tctcccagct ctagacaacc ctgcaaagga ctgtttttc ctgagcttgg ccagaagggg | 2859 |
| gccatgaggc ctcagtggac tttccacccc ctccctggcc tgttctgttt tgcctgaagt | 2919 |
| tggagtgagt gtggctcccc tctatttagc atgacaagcc ccaggcaggc tgtgcgctga | 2979 |
| caaccaccgc tccccagccc agggttcccc cagccctgtg aagggacta ggagcactgt | 3039 |
| agtaaatggc aattctttga cctcaacctg tgatgagggg aggaaactca cctgctggcc | 3099 |
| cctcacctgg gcacctgggg agtgggacag agtctgggtg tatttatttt cctccccagc | 3159 |
| aggtggggag ggggtttggg ggcttgcaag tatgttttag catgtgtttg gttctggggc | 3219 |
| cccttttac tccccttgag ctgagatgga acccttttgg cccccgagct gggggccatg | 3279 |
| agctccagac ccccagcaac cctcctatca cctcccctcc ttgcctcctg tgtaatcatt | 3339 |

```
tcttgggccc tcctgaaact tacacacaaa acgttaagtg atgaacatta aatagcaaag    3399
aaagaaaaat agtacaaaga g                                              3420
```

<210> SEQ ID NO 12
<211> LENGTH: 427
<212> TYPE: PRT
<213> ORGANISM: Homo sapiens

<400> SEQUENCE: 12

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350
```

-continued

```
Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 13
<211> LENGTH: 1731
<212> TYPE: DNA
<213> ORGANISM: Homo sapiens
<220> FEATURE:
<221> NAME/KEY: CDS
<222> LOCATION: (359)..(1303)
<300> PUBLICATION INFORMATION:
<308> DATABASE ACCESSION NUMBER: NM_002354.2
<309> DATABASE ENTRY DATE: 2015-03-15
<313> RELEVANT RESIDUES IN SEQ ID NO: (1)..(1731)

<400> SEQUENCE: 13
aactgcagcg ccggggctgg gggagggag cctactcact cccccaactc ccgggcggtg      60
actcatcaac gagcaccagc ggccagaggt gagcagtccc gggaaggggc cgagaggcgg    120
ggccgccagg tcgggcaggt gtgcgctccg ccccgccgcg cgcacagagc gctagtcctt    180
cggcgagcga gcaccttcga cgcggtccgg gaccccctc gtcgctgtcc tcccgacgcg     240
gacccgcgtg ccccaggcct cgcgctgccc ggccggctcc tcgtgtccca ctcccggcgc    300
acgccctccc gcgagtcccg ggcccctccc gcgcccctct tctcggcgcg cgcgcagc     358 atg gcg ccc ccg cag gtc ctc gcg ttc ggg ctt ctg ctt gcc gcg gcg       406
Met Ala Pro Pro Gln Val Leu Ala Phe Gly Leu Leu Leu Ala Ala Ala
1               5                   10                  15 acg gcg act ttt gcc gca gct cag gaa gaa tgt gtc tgt gaa aac tac       454
Thr Ala Thr Phe Ala Ala Ala Gln Glu Glu Cys Val Cys Glu Asn Tyr
            20                  25                  30 aag ctg gcc gta aac tgc ttt gtg aat aat aat cgt caa tgc cag tgt       502
Lys Leu Ala Val Asn Cys Phe Val Asn Asn Asn Arg Gln Cys Gln Cys
        35                  40                  45 act tca gtt ggt gca caa aat act gtc att tgc tca aag ctg gct gcc       550
Thr Ser Val Gly Ala Gln Asn Thr Val Ile Cys Ser Lys Leu Ala Ala
50                  55                  60 aaa tgt ttg gtg atg aag gca gaa atg aat ggc tca aaa ctt ggg aga       598
Lys Cys Leu Val Met Lys Ala Glu Met Asn Gly Ser Lys Leu Gly Arg
65                  70                  75                  80 aga gca aaa cct gaa ggg gcc ctc cag aac aat gat ggg ctt tat gat       646
Arg Ala Lys Pro Glu Gly Ala Leu Gln Asn Asn Asp Gly Leu Tyr Asp
                85                  90                  95 cct gac tgc gat gag agc ggg ctc ttt aag gcc aag cag tgc aac ggc       694
Pro Asp Cys Asp Glu Ser Gly Leu Phe Lys Ala Lys Gln Cys Asn Gly
            100                 105                 110 acc tcc atg tgc tgg tgt gtg aac act gct ggg gtc aga aga aca gac       742
Thr Ser Met Cys Trp Cys Val Asn Thr Ala Gly Val Arg Arg Thr Asp
        115                 120                 125 aag gac act gaa ata acc tgc tct gag cga gtg aga acc tac tgg atc       790
Lys Asp Thr Glu Ile Thr Cys Ser Glu Arg Val Arg Thr Tyr Trp Ile
    130                 135                 140 atc att gaa cta aaa cac aaa gca aga gaa aaa cct tat gat agt aaa       838
Ile Ile Glu Leu Lys His Lys Ala Arg Glu Lys Pro Tyr Asp Ser Lys
```

```
Ile Ile Glu Leu Lys His Lys Ala Arg Glu Lys Pro Tyr Asp Ser Lys
145                 150                 155                 160 agt ttg cgg act gca ctt cag aag gag atc aca acg cgt tat caa ctg      886
Ser Leu Arg Thr Ala Leu Gln Lys Glu Ile Thr Thr Arg Tyr Gln Leu
                165                 170                 175 gat cca aaa ttt atc acg agt att ttg tat gag aat aat gtt atc act      934
Asp Pro Lys Phe Ile Thr Ser Ile Leu Tyr Glu Asn Asn Val Ile Thr
            180                 185                 190 att gat ctg gtt caa aat tct tct caa aaa act cag aat gat gtg gac      982
Ile Asp Leu Val Gln Asn Ser Ser Gln Lys Thr Gln Asn Asp Val Asp
        195                 200                 205 ata gct gat gtg gct tat tat ttt gaa aaa gat gtt aaa ggt gaa tcc     1030
Ile Ala Asp Val Ala Tyr Tyr Phe Glu Lys Asp Val Lys Gly Glu Ser
    210                 215                 220 ttg ttt cat tct aag aaa atg gac ctg aca gta aat ggg gaa caa ctg     1078
Leu Phe His Ser Lys Lys Met Asp Leu Thr Val Asn Gly Glu Gln Leu
225                 230                 235                 240 gat ctg gat cct ggt caa act tta att tat tat gtt gat gaa aaa gca     1126
Asp Leu Asp Pro Gly Gln Thr Leu Ile Tyr Tyr Val Asp Glu Lys Ala
                245                 250                 255 cct gaa ttc tca atg cag ggt cta aaa gct ggt gtt att gct gtt att     1174
Pro Glu Phe Ser Met Gln Gly Leu Lys Ala Gly Val Ile Ala Val Ile
            260                 265                 270 gtg gtt gtg gtg ata gca gtt gtt gct gga att gtt gtg ctg gtt att     1222
Val Val Val Val Ile Ala Val Val Ala Gly Ile Val Val Leu Val Ile
        275                 280                 285 tcc aga aag aag aga atg gca aag tat gag aag gct gag ata aag gag     1270
Ser Arg Lys Lys Arg Met Ala Lys Tyr Glu Lys Ala Glu Ile Lys Glu
    290                 295                 300 atg ggt gag atg cat agg gaa ctc aat gca taa ctatataatt tgaagattat   1323
Met Gly Glu Met His Arg Glu Leu Asn Ala
305                 310 agaagaaggg aaatagcaaa tggacacaaa ttacaaatgt gtgtgcgtgg gacgaagaca   1383
tctttgaagg tcatgagttt gttagtttaa catcatatat ttgtaatagt gaaacctgta   1443
ctcaaaatat aagcagcttg aaactggctt taccaatctt gaaatttgac cacaagtgtc   1503
ttatatatgc agatctaatg taaaatccag aacttggact ccatcgttaa aattatttat   1563
gtgtaacatt caaatgtgtg cattaaatat gcttccacag taaaatctga aaaactgatt   1623
tgtgattgaa agctgccttt ctatttactt gagtcttgta catacatact ttttatgag    1683 ctatgaaata aaacatttta aactgaattt cttaaaaaaa aaaaaaaa                1731

<210> SEQ ID NO 14
<211> LENGTH: 314
<212> TYPE: PRT
<213> ORGANISM: Homo sapiens

<400> SEQUENCE: 14

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80
```

```
Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 15
<211> LENGTH: 12
<212> TYPE: PRT
<213> ORGANISM: Artificial Sequence
<220> FEATURE:
<223> OTHER INFORMATION: L803-mts / GSK-3beta peptidic inhibitor
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: AMIDATION

<400> SEQUENCE: 15

Gly Lys Glu Ala Pro Pro Ala Pro Pro Gln Ser Pro
1               5                   10
```

METHOD FOR PRODUCING RENAL PROGENITOR CELLS

CROSS-REFERENCE TO RELATED APPLICATIONS

This application is a National Stage application of PCT/JP2016/077353, filed Sep. 9, 2016, which claims priority from Japanese application JP 2015-179104, filed Sep. 11, 2015.

TECHNICAL FIELD

The present invention relates to a method for producing renal progenitor cells (RPCs) using a cell surface marker intended for acquiring and producing a high-purity RPC population from a RPC-containing cell population differentiated from pluripotent stem cells (PSCs).

BACKGROUND ART

The kidney is an important organ that functions to maintain good physical health through filtrating and removing toxic substances and waste products generated by metabolic activity in the body from the blood. Renal failure is a serious disease that impairs the function of the kidney, but since no effective drug therapy for this disease has yet been established, this disease is at present treated by renal transplantation, dialysis or the like. However, renal transplantation is faced with the problem of severe lack of donor organs, and dialysis also has the problems of the onset of complications and a heavy burden of medical costs; thus, there is a desire to develop a new therapy for this disease.

Meanwhile, there have already been reports on pluripotent cells, such as embryonic stem cells (ESCs), and induced pluripotent stem cells (iPSCs) obtained by introducing a reprogramming factor(s) into somatic cells (PTLs 1 and 2). Various studies have now been conducted to develop a new therapy for renal failure which involves transplantation of renal cells obtained by inducing differentiation of such PSCs. Another focus has been placed on developing a therapeutic drug for renal failure using homogeneous renal cells derived from such PSCs.

It is known that mammalian kidneys develop through the three stages of pronephros, mesonephros and metanephros, and that among them, the metanephros develops in the posterior region of intermediate mesoderm. In previous researches, a method for inducing differentiation of mouse PSCs into intermediate mesoderm was studied (NPL 1), and Odd-Skipped Related Transcription Factor 1 (OSR1) was identified as a characteristic marker of intermediate mesoderm. Also, SIX Homeobox 2 (SIX2) is known as one of factors characterizing RPCs (NPLs 2 and 3). As a result of the study with the human iPSCs (OSR1-GFP reporter human iPS cells) generated by introducing the green fluorescent protein (GFP) gene using a bacterial artificial chromosome (BAC) vector through homologous recombination with endogenous OSR1 allele, human PSCs were successfully induced to differentiate into intermediate mesoderm using Activin A, Wnt protein, bone morphogenetic protein (BMP) and various low-molecular compounds (NPL 3, PTL 3). Then, as a result of the study with OSR1-GFP & SIX2-tdTomato reporter human iPS cell lines generated by introducing the red fluorescent protein, tdTomato, into SIX2 loci in the OSR1-GFP reporter human iPS cell lines using the same homologous recombination procedure as adopted by Mae, et al. (NPL 3), a system for inducing differentiation of human PSCs into RPCs was successfully constructed, and the therapeutic efficacy of a therapy with the thus-obtained RPCs was confirmed in acute kidney injury models (NPL 4, PTL 4).

CITATION LIST

Patent Literatures

PTL 1: U.S. Pat. No. 5,843,780
PTL 2: WO 2007/069666
PTL 3: WO2012/011610
PTL 4: WO 2014/200115

Non Patent Literatures

NPL 1: Mae S, et al., Biochem. Biophys. Res. Commun., (2010), 393:877-882
NPL 2: Kobayashi A, et al., Cell Stem Cell, (2008), 3:169-181
NPL 3: Mae S, et al., Nat. Commun., (2013), 4:1367
NPL 4: Toyohara T, et al., Stem Cells Transl. Med, (2015), 4:980-992

SUMMARY OF INVENTION

Technical Problem

An object of the present invention resides in providing a method for acquiring and producing a high-purity RPC population from a RPC population into which PSCs are induced to differentiate, by identifying a cell surface marker specific to RPCs.

Solution to Problem

The present inventors have made intensive studies to achieve the aforementioned object, and as a result first found that a high-purity RPC population can be acquired and produced from a RPC-containing cell population by using a cell surface marker selected from CD9-negative (CD9 (−)), CD55-negative (CD55(−)), CD106-positive (CD106(+)), CD140a-positive (CD140a(+)), CD140b-positive (CD140b (+)), CD165-positive (CD165(+)), CD271-positive (CD271 (+)) and CD326-negative (CD326(−)). The present invention has been completed on the basis of this finding.

More specifically, the present invention has the characteristics defined below.

[1] A method for producing renal progenitor cells into which pluripotent stem cells are induced to differentiate, the method comprising the steps of:
(i) culturing the pluripotent stem cells under conditions that induce differentiation into renal progenitor cells; and
(ii) sorting a cell population from the cells obtained at step (i), by using at least one cell surface marker selected from the group consisting of CD9(−), CD55(−), CD106(+), CD140a(+), CD140b(+), CD165(+), CD271(+) and CD326 (−).
[2] The method as set forth in [1], wherein at step (ii), the sorting of a cell population is performed by using at least two cell surface markers.
[3] The method as set forth in [1], wherein at step (ii), the sorting of a cell population is performed by using at least three cell surface markers.
[4] The method as set forth in [1], wherein at step (ii), the sorting of a cell population is performed by using at least four cell surface markers.

[5] The method as set forth in [1], wherein at step (ii), at least two cell surface markers selected from the group consisting of CD9(−), CD140a(+), CD140b(+) and CD271(+) are used.
[6] The method as set forth in [5], wherein at step (ii), the sorting of a cell population is performed by using at least three cell surface markers.
[7] The method as set forth in [4], wherein at step (ii), CD9(−), CD140a(+), CD140b(+) and CD271(+) are used as the cell surface markers.
[8] The method as set forth in any of [1] to [7], wherein the pluripotent stem cells are induced pluripotent stem (iPS) cells.
[9] The method as set forth in any of [1] to [7], wherein the pluripotent stem cells are human iPS cells.
[10] A renal progenitor cell population produced by the method as set forth in any of [1] to [9].
[11] A method for sorting a cell population from a renal progenitor cell-containing cell population by using at least one cell surface marker selected from the group consisting of CD9(−), CD55(−), CD106(+), CD140a(+), CD140b(+), CD165(+), CD271(+) and CD326(−).
[12] The method as set forth in [11], wherein the sorting of a cell population is performed by using at least two cell surface markers.
[13] The method as set forth in [11], wherein the sorting of a cell population is performed by using at least three cell surface markers.
[14] The method as set forth in [11], wherein the sorting of a cell population is performed by using at least four cell surface markers.
[15] The method as set forth in [11], wherein at least two cell surface markers selected from the group consisting of CD9(−), CD140a(+), CD140b(+) and CD271(+) are used.
[16] The method as set forth in [15], wherein the sorting of a cell population is performed by using at least three cell surface markers.
[17] The method as set forth in [11], wherein CD9(−), CD140a(+), CD140b(+) and CD271(+) are used as the cell surface markers.
[18] The method as set forth in any of [11] to [17], wherein the renal progenitor cells are renal progenitor cells into which pluripotent stem cells are induced to differentiate.
[19] The method as set forth in any of [11] to [17], wherein the pluripotent stem cells are induced pluripotent stem (iPS) cells.
[20] The method as set forth in any of [11] to [17], wherein the pluripotent stem cells are human iPS cells.
[21] A cell population acquired by the method as set forth in any of [11] to [20].

Advantageous Effects of Invention

According to the present invention, it has first become possible to acquire and produce a high-purity RPC population from a RPC population into which PSCs (e.g., iPSCs) are induced to differentiate, by using a cell surface marker. The RPC population acquired by the method of this invention can be used in regenerative medicine for renal diseases such as renal failure.

BRIEF DESCRIPTION OF DRAWINGS

The application file contains at least one drawing executed in color. Copies of this patent application publication with color drawing(s) will be provided by the Office upon request and payment of the necessary fee.

FIG. 1 shows a set of two-dimensional scatter plots of the flow cytometric measurements of the expression of CD9, CD55, CD106, CD140a, CD140b, CD165, CD271 and CD326 versus OSR1 and SIX2. The y-axis represents the fluorescence intensity of an antibody against each of the different cell surface markers, and the x-axis represents the fluorescence intensity of a fluorescence reporter representative of OSR1 or SIX2 protein expression.

FIG. 2 shows the results of the sorting of CD9(−)CD140a (+)CD140b(+)CD271(+) cells from hiPSC-derived differentiated cell groups as performed in Example 2. FIG. 2A shows a set of flow cytograms for hiPSCs-derived differentiated cell groups stained with CD9, CD140a, CD140b and CD271. The y- and x-axes represent the fluorescence intensities of antibodies against different cell surface markers. P6 depicts the presence of a CD9(−)CD140a(+) cell population; P4 depicts the presence of a CD9(−)CD140b(+) cell population; and P3 depicts the presence of a CD9(−)CD271(+) cell population. The P3+P4+P6 cell population depicted in FIG. 2A was fractionated. FIG. 2B shows a set of two-dimensional scatter plots of the flow cytometric measurements of OSR1 and SIX2 expression in hiPSCs before differentiation induction, in hiPSC-derived differentiated cell groups, and in the P3+P4+P6 cell population sorted from the hiPSC-derived differentiated cell groups, respectively in order from left to right panels. The y- and x-axes represent the fluorescence intensities of fluorescence reporters representative of OSR1 or SIX2 protein expression. The percent values shown represent the percentages of OSR1/SIX2 double-positive cells (OSR1(+)SIX2(+) cells; upper right fraction), OSR1-positive, SIX2-negative cells (OSR1(+)SIX2(−) cells; upper left fraction), OSR1-negative, SIX2-positive cells (OSR1(−)SIX2(+) cells; lower right fraction), and OSR1/SIX2 double-negative cells (OSR1(−)SIX2(−) cells; lower left fraction).

FIG. 3 shows an example of the proximal renal tubule-like structures prepared in Example 3 from the CD9(−)CD140a (+)CD40b(+)CD271(+) cells fractionated from hiPSC-derived differentiated cell groups. FIG. 3A illustrates the differentiation procedure into proximal renal tubule, in which cell aggregates are formed and cocultured with Wnt4-expressing NIH3T3 fibroblasts according to the same procedure as disclosed in NPL 4. Cell aggregates composed of $1\times10^5$ cells were formed using a mouse ureteric bud cell (UBC)-conditioned medium supplemented with BMP7 and the Rho-kinase inhibitor Y-27632 (Wako; Cat. No. 253-00513). The next day, the culture medium was replaced with a mouse UBC-conditioned medium supplemented with BMP7, Y-27632, and the GSK-3β inhibitor BIO (Wako; Cat. No. 029-16241), and the cells were further cultured for one day and then cocultured on top of Wnt4-expressing NIH3T3 fibroblasts treated with mitomycin C to induce the cells to differentiate into proximal renal tubule. FIG. 3B shows a microscopic image (upper left panel) of CD9(−)CD140a(+) CD140b(+)CD271(+) cell aggregates after coculture with Wnt4-expressing NIH3T3 fibroblasts, immunostaining images (upper right and lower left panels) of said cell aggregates, and a merged image of these images (lower right panel). Further, Lotus Tetragonolobus Lectin (LTL)-expressing cells are shown in enlarged views indicated by arrows. In these panels, LTL is a proximal renal tubule marker, Hoechst33342 is a cell nuclear staining dye, and the scale bar represents 100 μm.

FIG. 4 shows the percentages of OSR1(+)SIX2(+) cells, OSR1(+)SIX2(−) cells, OSR1(−)SIX2(+) cells, and OSR1 (−)SIX2(−) cells in cell populations sorted in Example 4 by all exhaustive combinations of the negative selection marker CD9 with any three of the positive selection markers. This figure also shows the percentages of OSR1(+)SIX2(+) cells, OSR1(+)SIX2(−) cells, OSR1(−)SIX2(+) cells, and OSR1(−)SIX2(−) cells in cell populations sorted by other marker combinations in which the negative selection marker CD55 or CD326 was used instead of CD9.

FIG. 5 shows the following cell percentages: the percentage of OSR1(+)SIX2(+) cells in cell populations collected in Example 5 from an unsorted cell population using any combination of the cell surface markers CD9(−), CD140a(+), CD140b(+) and CD271(+); the percentage of cells demarcated by each of different cell marker combinations in the unsorted cell population; and the percentage of the number of OSR1(+)SIX2(+) cells collected using each of different surface marker combinations with respect to the number of unsorted cells.

FIG. 6 shows the results of inducing differentiation of a cell population sorted from a hiPSC 201B7 line-derived differentiated cell population using CD9(−)CD140a(+)CD140b(+)CD271(+) as an indicator into proximal renal tubule-like structures in Example 6. FIG. 6A shows a set of histograms of the number of cells as a function of the fluorescence intensity of each of OSR1 (detected by GFP), SIX2 (detected by tdTomato) and the different cell surface markers. FIG. 6B shows a set of scatter plots of the flow cytometric measurements of the expression of CD9 v.s. CD140a, CD140b or CD271 in an iPSC 201B7 line-derived differentiated cell population. The y- and x-axes represent the fluorescence intensities of antibodies against different cell surface markers. CD9(−)CD140a(+)CD140b(+)CD271(+) cells were fractionated by sorting of gating (P4+P2+P3) fractions. FIG. 6C shows a merged image of the microscopic and immunostaining images of sorted CD9(−)CD140a(+)CD140b(+)CD271(+) cell aggregates after coculture with Wnt4-expressing NIH3T3 fibroblasts. In this panel, LTL is a proximal renal tubule marker (boxed), and the scale bar represents 100 μm.

FIG. 7 shows the results of immunostaining of an iPSC 201B7 line-derived differentiated cell population with anti-SIX2 antibodies as performed in Example 7. FIG. 7A shows a set of immunostaining images of an unsorted cell population, and FIG. 7B shows a set of immunostaining images of a cell population sorted using CD9(−)CD140a(+)CD140b(+)CD271(+) as an indicator. In these panels, the white solid arrows represent SIX2-positive cells, and the white outline arrows represent SIX2-negative cells. The scale bar represents 100 μm. In both of FIGS. 7A and 7B, the left panel shows a light field image, the central panel shows an anti-SIX2 antibody-staining image, and the right panel shows a Hoechst33342 nuclear staining image.

DESCRIPTION OF EMBODIMENTS

Hereunder, the present invention will be described in detail.

The present invention provides a method for acquiring and producing a high-purity RPC population from a RPC population into which PSCs are induced to differentiate, by using a cell surface marker. To be specific, this invention includes the following method (hereinafter also referred to as "the production method of the present (this) invention"):

"A method for producing a renal progenitor cell population into which pluripotent stem cells are induced to differentiate, the method comprising the steps of:
(i) culturing the pluripotent stem cells under conditions that induce differentiation into renal progenitor cells; and
(ii) sorting a cell population from the cells obtained at step (i), by using at least one cell surface marker selected from the group consisting of CD9(−), CD55(−), CD106(+), CD140a(+), CD140b(+), CD165(+), CD271(+) and CD326(−)."

The present invention also provides a method for sorting a cell population from a RPC-containing cell population using a cell surface marker. To be specific, this invention includes the following method (hereinafter also referred to as "the sorting method of the present (this) invention"):

"A method for sorting a cell population from a renal progenitor cell-containing cell population using at least one cell surface marker selected from the group consisting of CD9(−), CD55(−), CD106(+), CD140a(+), CD140b(+), CD165(+), CD271(+) and CD326(−)."

The present invention includes a renal progenitor cell population produced by the production method of this invention.

The present invention also includes a cell population acquired by the sorting method of this invention.

The following provides descriptions of the present invention.

1. Step (i) of Culturing PSCs Under Conditions that Induce Differentiation into a RPC Population:

The procedure for inducing differentiation of PSCs into a RPC population, which can be used at this step, can be any procedure including but not limited to those disclosed in NPL 4 and PTL 4. At step (i), it is only necessary to obtain a cell population containing RPCs, since RPCs can be concentrated by the subsequent sorting at step (ii). The percent content of RPCs in the cell population obtained at step (i) is not of particular importance, and is, for example, not less than 5%, not less than 10%, not less than 15%, not less than 20%, not less than 25%, or not less than 30%.

In the present invention, RPCs are produced as a cell population of concentrated RPCs. The percent content of RPCs in the produced cell population is not particularly limited, and is, for example, not less than 50%, not less than 60%, not less than 65%, not less than 70%, not less than 71%, not less than 72%, not less than 73%, not less than 74%, or not less than 75%. Accordingly, as referred to in this invention, "sorting" means obtaining a cell population containing desired cells at a concentration of not less than 50%, not less than 60%, not less than 65%, not less than 70%, not less than 71%, not less than 72%, not less than 73%, not less than 74%, or not less than 75%.

As referred to in the present invention, the "renal progenitor cells (RPCs)" refers to cells partially transforming into renal tubule, and to OSR1/SIX2 double-positive (OSR1(+)SIX2(+)) cells. As an example, OSR1 is a protein encoded by the human OSR1 gene (NCBI Accession No. NM_145260.2), and SIX2 is a protein encoded by the human SIX2 gene (NCBI Accession No. NM_016932.4). "OSR1-positive (OSR1(+))" means that OSR1 transcription activity is high, and more specifically means, for example, that OSR1 mRNA can be detected by a known method, that OSR1 protein can be detected by a known method (Examples 1, 2 and 4-6), or that the expression of a marker gene functionally linked to OSR1 promoter can be observed. Likewise, "SIX2-positive (SIX2(+))" means that SIX2 transcription activity is high, and more specifically means, for example, that SIX2 mRNA can be detected by a known method, that SIX2 protein can be detected by a known method (Examples 1, 2 and 4-6), or that the expression of a marker gene functionally linked to SIX2 promoter can be observed. As referred to in this invention, the "marker gene" refers to, for example, but is not limited to, a gene encoding a fluorescent protein.

As referred to in the present invention, the "pluripotent stem cells (PSCs)" refers to stem cells that not only have pluripotency, which is an ability to differentiate into many types of cells with different properties and morphologies as found in living organisms, but also have proliferative ability, and this term includes any types of cells that are able to be induced into RPCs. Examples of PSCs include, but are not particularly limited to, embryonic stem cells (ESCs), nuclear transfer embryonic stem cells (ntESCs), which are produced by using a nuclea transfer technique, germline stem cells (GSCs), embryonic germ cells (EGCs), induced pluripotent stem cells (iPSCs), and pluripotent cells derived from cultured fibroblasts or myeloid stem cells (multi-lineage differentiating stress enduring cells; Muse cells). Preferred PSCs are iPSCs, more preferably human iPSCs, from the viewpoint that such cells can be acquired without destroying the embryo, ovum or the like during the cell production process.

The methods for producing iPSCs are already known in the art, and iPSCs can be produced by introducing a reprogramming factor(s) into any type of somatic cells. As referred to herein, the "reprogramming factor(s)" refers to a gene(s) or gene product(s), such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3 or Glis1. Such reprogramming factors may be used alone or in combination. Exemplary combinations of reprogramming factors include those combinations disclosed in each of the following literatures: WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al., *Nat. Biotechnol.*, (2008), 26: 795-797; Shi Y, et al., *Cell Stem Cell*, (2008), 2: 525-528; Eminli S, et al., *Stem Cells*, (2008), 26:2467-2474; Huangfu D, et al., *Nat. Biotechnol.*, (2008), 26:1269-1275; Shi Y, et al., *Cell Stem Cell*, (2008), 3: 568-574; Zhao Y, et al., *Cell Stem Cell*, (2008), 3:475-479; Marson A, *Cell Stem Cell*, (2008), 3: 132-135; Feng B, et al., *Nat. Cell Biol.*, (2009), 11:197-203; R. L. Judson et al., *Nat. Biotechnol.*, (2009), 27:459-461; Lyssiotis C. A., et al., *Proc. Natl. Acad Sci. USA*, (2009), 106:8912-8917; Kim J. B., et al., *Nature*, (2009), 461:649-643; Ichida J. K., et al., *Cell Stem Cell*, (2009), 5:491-503; Heng J. C., et al., *Cell Stem Cell*, (2010), 6:167-174; Han J, et al., *Nature*, (2010), 463:1096-1100; Mali P, et al., *Stem Cells*, (2010), 28:713-720; and Maekawa M, et al., *Nature*, (2011), 474:225-229.

Non-limiting examples of somatic cells include not only all types of somatic cells from neonates and from healthy or affected individuals, but also all types of primary cultured cells, passaged cells and established cells derived from the aforementioned somatic cells. Specific examples of somatic cells include: (1) tissue stem cells (somatic stem cells), such as neural stem cells, hematopoietic stem cells, mesenchymal stem cells, and dental pulp stem cells; (2) tissue progenitor cells; and (3) differentiated cells found in organs and tissues, such as blood cells (e.g., peripheral blood cells, cord blood cells), muscle cells, skin cells, hair cells, hepatic cells, gastric mucosal cells, intestinal cells, splenic cells, pancreatic cells, brain cells, pulmonary cells, renal cells, and fat cells.

When iPSCs are used as a material for transplant cells, it is desirable to use somatic cells having the same, or substantially the same, human leucocyte antigen (HLA) genotype as a transplantation recipient, from the viewpoint that no episode of transplant rejection can occur. As referred to herein, the wording "substantially the same" in relation to human leucocyte antigen (HLA) genotype means that somatic cells have a matching in HLA genotype to such an extent that immune response to transplanted cells can be suppressed with an immune suppressor. Examples of such somatic cells include those cells with the same HLA type at the three different loci of HLA-A, HLA-B and HLA-DR, or at the four different loci of HLA-A, HLA-B, HLA-DR and HLA-C.

In one embodiment, step (i) is performed using the procedure for inducing differentiation of PSCs into a RPC population as disclosed in NPL 4 and PTL 4. To be specific, step (i) involves the following steps (i-1) to (i-3):

(i-1) culturing PSCs in a culture medium supplemented with at least one substance selected from Activin A, GSK-3β inhibitors, and retinoic acid derivatives;

(i-2) culturing a cell population obtained at step (i-1), in a culture medium supplemented with at least one substance selected from BMP7, GSK-3β inhibitors, and retinoic acid derivatives; and (i-3) culturing a cell population obtained at step (i-2), in a culture medium supplemented with a TGFβ signal stimulator and a BMP inhibitor.

The following provides descriptions of steps (i-1) to (i-3).

Step (i-1) of culturing PSCs in a culture medium supplemented with at least one substance selected from Activin A, GSK-3β inhibitors, and retinoic acid derivatives:

At this step, PSCs may be dissociated by any procedure known in the art and cultured by suspension culture or adhesion culture. Exemplary PSC dissociation procedures include mechanical dissociation, and dissociation using a dissociation solution with proteolytic and collagenolytic activities (e.g., Accutase® and Accumax (Innovative Cell Technologies, Inc.)) or a dissociation solution with only collagenolytic activity. Preferred is a procedure in which PSCs are dissociated using a dissociation solution with proteolytic and collagenolytic activities and finely dispersed mechanically into single cells. The human PSCs to be preferably used at this step are PSC colonies cultured to 80% confluence per culture dish used.

The suspension culture to be used in the method of the present invention refers to culturing of cells while they are not adhered to a culture dish. The suspension culture can be performed, but is not particularly limited to, using a vessel not artificially treated (e.g., with extracellular matrix coating) to enhance the adhesion to cells, or a vessel artificially treated (e.g., with poly(hydroxyethyl methacrylate) (poly-HEMA) coating) to prevent adhesion.

The adhesion culture to be used in the method of the present invention refers to culturing of cells while they are adhered to a culture dish. The adhesion culture can also be performed, but is not particularly limited to, in a coated culture dish. Exemplary coating agents include matrigel (BD Biosciences), Synthemax® (Corning), collagen, gelatin, laminin, heparan sulfate proteoglycan or entactin, and combinations thereof, with preference being given to matrigel, Synthemax® or gelatin.

The culture medium to be used at step (i-1) can be prepared by adding at least one substance selected from Activin A, GSK-3β inhibitors, and retinoic acid derivatives to a basal medium for use in culturing animal cells. In one embodiment, the substances used at this step are a combination of Activin A and a GSK-3β inhibitor, or a combination of a GSK-3β inhibitor and a retinoic acid derivative. Examples of the basal medium include Iscove's modified Dulbecco's medium (IMDM), Medium 199, Eagle's minimum essential medium (EMEM), alpha-modified Eagle's minimum essential medium (αMEM), Dulbecco's modified Eagle's medium (DMEM), Ham's F12 (F12) medium, RPMI 1640 medium, Fischer's medium, and mixed media thereof. The culture medium may be supplemented with serum (e.g., fetal bovine serum (FBS)) or may be serum-free. Depending on the need, the culture medium may be supplanted with at least one serum alternative such as albumin, knockout serum replacement (KSR) (Invitrogen), N2 supplement (Invitrogen), and/or B27 supplement (Invitrogen), or may also be supplemented with at least one substance such as transferrin, fatty acids, insulin, collagen precursors, trace elements, 2-mercaptoethanol, 3'-thiol glycerol, lipids, amino acids, L-glutamine, GlutaMAX (Invitrogen), non-essential amino acids (NEAAs), vitamins, growth factors, low-molecular compounds, antibiotics, antioxidants, pyruvic acid, buffers, and/or inorganic salts. In one embodiment of this step, the basal medium is a DMEM/F12 (1:1) mixed medium supplemented with GlutaMAX, serum and an antibiotic.

Examples of Activin A that can be used at step (i-1) include Activin A proteins derived from humans and other animals, and functional variants thereof, as exemplified by Activin A products commercially available from R&D Systems and other manufacturers. The concentration of Activin A used at this step is in the range of 1 ng/mL to 1000 ng/mL, preferably 10 ng/mL to 500 ng/mL, more preferably 50 ng/mL to 200 ng/mL.

The GSK-3β inhibitor to be used at step (i-1) is not particularly limited as long as it is capable of inhibiting GSK-3β functions such as kinase activity. Exemplary GSK-3β inhibitors include: the indirubin derivative BIO (also named as GSK-3β Inhibitor IX; 6-bromoindirubin-3'-oxime); the maleimide derivative SB216763 (3-(2,4-dichlorophenyl)-4-(1-methyl-1H-indol-3-yl)-1H-pyrrole-2,5-dione); the phenyl α-bromomethyl ketone compound GSK-3D Inhibitor VII (2,4'-dibromoacetophenone); the cell membrane-permeable phosphorylation peptide L803-mts (also named as GSK-3β Peptide Inhibitor, Myr-N-GKEAPPAP-PQSpP-NH2 (SEQ ID NO:15)); and the highly selective GSK inhibitor CHIR99021 (6-[[2-[[4-(2,4-dichlorophenyl)-5-(5-methyl-1H-imidazol-2-yl)-2-pyrimidinyl]amino]ethyl]amino]-3-pyridinecarbonitrile) (*Nature*, (2008), 453: 519-523). The compounds listed above are available from Stemgent, Calbiochem, Biomol and other manufacturers, or may be prepared on one's own. A preferred example of the GSK-3β inhibitor to be used at this step is CHIR99021. The concentration of the GSK-3β inhibitor used at this step can be selected by one skilled in the art as appropriate depending on the type of the GSK-3β inhibitor to be used. For example, when CHIR99021 is used as a GSK-3β inhibitor, the concentration of this inhibitor is in the range of 0.01 μM to 100 μM, preferably 0.1 μM to 10 μM, more preferably 1 μM to 3 μM.

The retinoic acid derivative to be used at step (i-1) is an optionally artificially modified retinoic acid that maintains the functions of naturally occurring retinoic acid. Exemplary retinoic acid derivatives include retinoid compounds and vitamin A compounds. Examples of retinoid compounds include retinoic acids, 3-dehydroretinoic acid, 4-[[(5,6,7,8-tetrahydro-5,5,8,8-tetramethyl-2-naphthalenyl)carbonyl]amino]-benzoic acid (AM580) (Tamura K, et al., *Cell Differ. Dev.*, (1990), 32: 17-26), 4-[(1E)-2-(5,6,7,8-tetrahydro-5,5,8,8-tetramethyl-2-naphthalenyl)-1-propen-1-yl]-benzoic acid (TTNPB) (Strickland S, et al., *Cancer Res.*, (1983), 43: 5268-5272), those retinoid compounds disclosed in Takenaga, K. et al., *Cancer Res.*, (1980), 40: 914-919, retinol palmitate, retinol, retinal, 3-dehydroretinol, and 3-dehydroretinal. Retinoic acid compounds refer to retinoid compounds having a carboxyl group, as exemplified by retinoic acids, 3-dehydroretinoic acid, AM580, and TTNPB. In one embodiment of this step, the retinoic acid derivative is a retinoid compound or a vitamin A compound. In another embodiment of this step, the retinoic acid derivative is a retinoic acid compound. In yet another embodiment of this step, the retinoic acid derivative is a vitamin A compound. A preferred example of the retinoic acid derivative to be used at this step is AM580 or TTNPB. The concentration of the retinoic acid derivative used at this step can be selected by one skilled in the art as appropriate depending on the type of the retinoic acid derivative to be used. For example, when AM580 or TTNPB is used as a retinoic acid derivative, the concentration of this derivative is in the range of 0.01 μM to 100 μM, preferably 0.1 μM to 10 μM, more preferably 0.5 μM to 2 μM.

The culture medium used at step (i-1) may be further supplemented with a ROCK inhibitor. In particular, when this step involves dispersing PSCs into single cells, it is preferred that the culture medium be supplemented with a ROCK inhibitor.

The type of a ROCK inhibitor is not particularly limited as long as it is capable of inhibiting the functions of Rho-kinase (ROCK). Exemplary ROCK inhibitors include Y-27632 (e.g., Ishizaki et al., *Mol. Pharmacol.*, (2000), 57, 976-983; Narumiya et al., *Methods Enzymol.*, (2000), 325, 273-284), Fasudil/HA1077 (e.g., Uehata et al., *Nature*, (1997), 389: 990-994), H-1152 (e.g., Sasaki et al., *Pharmacol. Ther.*, (2002), 93: 225-232), Wf-536 (e.g., Nakajima et al., *Cancer Chemother. Pharmacol.*, (2003), 52(4): 319-324) and derivatives thereof, as well as antisense nucleic acids, RNA interference-triggering nucleic acids (e.g., siRNA) and dominant-negative variants, which target ROCK, and expression vectors thereof. Other known low-molecular compounds can also be used as ROCK inhibitors (refer to, e.g., U.S. Patent Application Publication Nos. US 2005/0209261, US 2005/0192304, US 2004/0014755, US 2004/0002508, US 2004/0002507, US 2003/0125344 and US 2003/0087919, and International Patent Publication Nos. WO 2003/062227, WO 2003/059913, WO 2003/062225, WO 2002/076976 and WO 2004/039796). In the present invention, one or two or more ROCK inhibitors can be used. A preferred example of the ROCK inhibitor to be used at this step is Y-27632. The concentration of the ROCK inhibitor used at this step can be selected by one skilled in the art as appropriate depending on the type of the ROCK inhibitor to be used. For example, when Y-27632 is used as a ROCK inhibitor, the concentration of this inhibitor is in the range of 0.1 μM to 100 μM, preferably 1 μM to 50 μM, more preferably 5 μM to 20 μM.

The cell culture at step (i-1) is performed at a culture temperature of, but not limited to, about 30 to 40° C., preferably about 37° C., and in an atmosphere of $CO_2$-containing air. The $CO_2$ concentration is in the range of about 2 to 5%, preferably about 5%. The culture period at this step is for example not longer than 2 days, preferably 2 days.

Step (i-2) of culturing a cell population obtained at step (i-1), in a culture medium supplemented with at least one substance selected from BMP7, GSK-3β inhibitors, and retinoic acid derivatives:

At this step, the population of suspension cultured cells obtained at step (i-1) described above may be adhesion cultured, as it is, in a given culture medium in a coated culture dish, or the population of adhesion cultured cells obtained at step (i-1) may be continued to be cultured through replacement of a culture medium.

The culture medium to be used at step (i-2) can be prepared by adding at least one substance selected from BMP7, GSK-3β inhibitors, and retinoic acid derivatives to a basal medium for use in culturing animal cells. In one embodiment, the substance(s) used at this step is(are) a combination of BMP7 and a GSK-3β inhibitor, or a retinoic acid derivative. Examples of the basal medium include IMDM, Medium 199, EMEM, αMEM, DMEM, Ham's F12 medium, RPMI 1640 medium, Fischer's medium, and mixed media thereof. The culture medium may be supplemented with serum (e.g., FBS) or may be serum-free. Depending on the need, the culture medium may be supplanted with at least one serum alternative such as albumin, KSR (Invitrogen), N2 supplement (Invitrogen), and/or B27 supplement (Invitrogen), or may also be supplemented with at least one substance such as transferrin, fatty acids, insulin, collagen precursors, trace elements, 2-mercaptoethanol, 3'-thiol glycerol, lipids, amino acids, L-glutamine, GlutaMAX (Invitrogen), non-essential amino acids (NEAAs), vitamins, growth factors, antibiotics, antioxidants, pyruvic acid, buffers, inorganic salts and equivalents thereto. In one embodiment of this step, the basal medium is a DMEM/F12 medium supplemented with GlutaMAX, KSR, NEAAs, 2-mercaptoethanol and an antibiotic.

At step (i-2), for example, the cell population obtained at step (i-1) may be cultured in a culture medium supplemented with at least one substance selected from BMP7 and GSK-30 inhibitors, and then further cultured in a culture medium supplemented with a retinoic acid derivative. Preferably, step (i-2) involves culturing the cell population obtained at step (i-1), in a culture medium supplemented with at least one substance selected from BMP7 and GSK-30 inhibitors, and then further culturing the cell population in a culture medium supplemented with a retinoic acid derivative and a TGFβ signal stimulator. In other words, step (i-2) may be performed by taking the following two separate steps (i-2-a) and (i-2-b):

(i-2-a) culturing the cell population in a culture medium supplemented with at least one substance selected from BMP7 and GSK-3β inhibitors; and (i-2-b) culturing the cell population in a culture medium supplemented with a retinoic acid derivative and a TGFβ signal stimulator.

More preferably, step (i-2) involves the step (i-2-a) of culturing the cell population in a culture medium supplemented with BMP7 and a GSK-3β inhibitor, and the step (i-2-b) of culturing the cell population in a culture medium supplemented with a retinoic acid derivative and a TGFβ signal stimulator.

Examples of BMP7 that can be used at step (i-2) include human BMP7 (NCBI Accession No. NM_001719.2) and BMP7 proteins derived from other animals, and functional variants thereof (variants that maintain a differentiation induction ability), as exemplified by BMP7 products commercially available from Invitrogen, R&D Systems and other manufacturers. The concentration of BMP7 used at this step is in the range of 1 ng/mL to 1000 ng/mL, preferably 10 ng/mL to 500 ng/mL, more preferably 50 ng/mL to 200 ng/mL.

Examples of the GSK-3β inhibitor that can be used at step (i-2) include those inhibitors mentioned above in relation to step (i-1). A preferred example of the GSK-3β inhibitor is CHIR99021. The concentration of the GSK-3β inhibitor used at this step can be selected by one skilled in the art as appropriate depending on the type of the GSK-3β inhibitor to be used. For example, when CHIR99021 is used as a GSK-3β inhibitor, the concentration of this inhibitor is in the range of 0.01 μM to 100 μM, preferably 0.1 μM to 10 μM, more preferably 1 μM to 3 μM.

Examples of the retinoic acid derivative that can be used at step (i-2) include those derivatives mentioned above in relation to step (i-1). A preferred example of the retinoic acid derivative is AM580 or TTNPB. The concentration of the retinoic acid derivative used at this step can be selected by one skilled in the art as appropriate depending on the type of the retinoic acid derivative to be used. For example, when AM580 or TTNPB is used as a retinoic acid derivative, the concentration of this derivative is in the range of 0.01 μM to 100 μM, preferably 0.1 μM to 10 μM, more preferably 0.5 μM to 2 μM.

The type of the TGFβ signal stimulator to be used at step (i-2) is not particularly limited as long as it is capable of activating TGFβ3 signal pathway. Exemplary TGFβ signal stimulators include proteins such as TGFβ1, TGFβ2 and TGFβ3 (available from Peprotech, R&D, and other manufacturers), and compounds such as IDE1 (1-[2-[(2-carboxyphenyl)methylene]hydrazide]heptanoic acid) and IDE2 (1-(2-cyclopentylidenehydrazide)-heptanedioic acid) (Borowiak M, et al., *Cell Stem Cell*, (2009), 4: 348-358). IDE1 and IDE2 are available from Stemgent, Tocris and other manufacturers. A preferred example of the TGFβ signal stimulator is TGFβ1. The concentration of the TGFβ signal stimulator used at this step can be selected by one skilled in the art as appropriate depending on the type of the TGFβ signal stimulator to be used. For example, when any of proteins such as TGFβ1, TGFβ2 and TGFβ3 is used as a TGFβ signal stimulator, the concentration of this stimulator is in the range of 0.1 ng/mL to 100 ng/mL, preferably 1 ng/mL to 10 ng/mL, more preferably 5 ng/mL to 10 ng/mL. When any of IDE1 and IDE2 is used as a TGFβ signal stimulator, the concentration of this stimulator is in the range of 1 μM to 100 μM, preferably 25 μM to 75 μM, more preferably 40 μM to 60 μM.

The cell culture at step (i-2) is performed at a culture temperature of, but not limited to, about 30 to 40° C., preferably about 37° C., and in an atmosphere of $CO_2$-containing air. The $CO_2$ concentration is in the range of about 2 to 5%, preferably about 5%. The culture period at this step is for example not shorter than 3 days, preferably not shorter than 3 days and not longer than 12 days, more preferably not shorter than 3 days and not longer than 9 days. During this step, it is desirable to replace a culture medium every 3 days. When step (i-2) involves steps (i-2-a) and (i-2-b), the total culture period at step (i-2) is as described above, and more particularly, the culture period at step (i-2-a) is for example not shorter than 1 day, preferably not shorter than 2 days and not longer than 11 days, more preferably not shorter than 2 days and not longer than 6 days, and the culture period at step (i-2-b) is for example not shorter than 1 day, preferably not shorter than 2 days and not longer than 11 days, more preferably not shorter than 3 days and not longer than 6 days. During these steps, it is desirable to replace a culture medium every 3 days.

By taking the steps (i-1) and (i-2) as described above, PSCs can be induced into intermediate mesodermal cells. OSR1 is known as a marker characterizing intermediate mesodermal cells. In one embodiment, a cell population induced by following steps (i-1) and (i-2) contains a large number of OSR1-positive SIX2-negative (OSR1(+)SIX2(−)) intermediate mesodermal cells, but may also contain OSR1/SIX2 double-positive (OSR1(+)SIX2(+)) renal progenitor cells. Accordingly, step (i) may be completed by taking the steps (i-1) and (i-2) as described above, but from the viewpoint of increasing the content of RPCs, it is desirable to take not only the above two steps but also step (i-3).

Step (i-3) of culturing the cell population obtained at step (i-2), in a culture medium supplemented with a TGFβ signal stimulator and a BMP inhibitor:

At this step, the (intermediate mesodermal) cell population obtained at steps (i-1) and (i-2) as described above can be cultured by suspension or adhesion culture as they are, or after being dissociated by any procedure known in the art. Exemplary cell dissociation procedures include mechanical dissociation, and dissociation using a dissociation solution with proteolytic and collagenolytic activities (e.g., Accutase® and Accumax (Innovative Cell Technologies, Inc.)) or a dissociation solution with only collagenolytic activity.

The culture medium to be used at step (i-3) can be prepared by adding a TGFβ signal stimulator and a BMP inhibitor to a basal medium for use in culturing animal cells. Examples of the basal medium include IMDM, Medium 199, EMEM, αMEM, DMEM, Ham's F12 medium, RPMI 1640 medium, Fischer's medium, and mixed media thereof. The culture medium may be supplemented with serum (e.g., FBS) or may be serum-free. Depending on the need, the culture medium may be supplanted with at least one serum alternative such as albumin, KSR (Invitrogen), N2 supplement (Invitrogen), and/or B27 supplement (Invitrogen), or may also be supplemented with at least one substance such as transferrin, fatty acids, insulin, collagen precursors, trace elements, 2-mercaptoethanol, 3'-thiol glycerol, lipids, amino acids, L-glutamine, GlutaMAX (Invitrogen), non-essential amino acids (NEAAs), vitamins, growth factors, antibiotics, antioxidants, pyruvic acid, buffers, inorganic salts and equivalents thereto. In one embodiment of this step, the basal medium is a DMEM/F12 medium supplemented with GlutaMAX, KSR, NEAAs, 2-mercaptoethanol and an antibiotic.

The type of the TGFβ3 signal stimulator to be used at step (i-3) is not particularly limited as long as it is capable of activating TGFβ signal pathway. Exemplary TGFβ signal stimulators include proteins such as TGFβ1, TGFβ2 and TGFβ3, and compounds such as IDE1 and IDE2. A preferred example of the TGFβ signal stimulator is TGFβ1. The concentration of the TGFβ signal stimulator used at this step can be selected by one skilled in the art as appropriate depending on the type of the TGFβ3 signal stimulator to be used. For example, when any of proteins such as TGFβ1, TGFβ2 and TGFβ3 is used as a TGFβ3 signal stimulator, the concentration of this stimulator is in the range of 0.1 ng/mL to 100 ng/mL, preferably 1 ng/mL to 10 ng/mL, more preferably 5 ng/mL to 10 ng/mL. When any of IDE1 and IDE2 is used as a TGFβ signal stimulator, the concentration of this stimulator is in the range of 1 μM to 100 μM, preferably 25 μM to 75 μM, more preferably 40 μM to 60 μM.

The type of the BMP inhibitor to be used at step (i-3) is not particularly limited as long as it is capable of activating BMP signal pathway. Exemplary BMP inhibitors include proteinaceous inhibitors such as chordin, noggin and follistatin, dorsomorphin (6-[4-(2-piperidin-1-yl-ethoxy)phenyl]-3-pyridin-4-yl-pyrazolo[1,5-a]pyrimidine) and derivatives thereof (Yu et al., *Circulation*, (2007), 116:II_60; Yu et al., *Nat. Chem. Biol.*, (2008), 4:33-41; J. Hao et al., *PLoS ONE*, (2008), 3:e2904), DMH1 (4-[6-(4-isopropoxyphenyl) pyrazolo[1,5-a]pyrimidin-3-yl]quinoline, 4-[6-[4-(1-methylethoxy)phenyl]pyrazolo[1,5-a]pyrimidin-3-yl]quinoline), and LDN193189 (4-(6-(4-(piperidin-1-yl)phenyl)pyrazolo[1,5-a]pyrimidin-3-yl)quinoline). The compounds listed above are available from Stemgent, Tocris Bioscience, Merck Life Science, Wako, and other manufacturers, or may be prepared on one's own. Preferred examples of the BMP inhibitor include DMH1, LDN193189, noggin, and dorsomorphin, and a more preferred example thereof is DMH1. The concentration of the BMP inhibitor used at this step can be selected by one skilled in the art as appropriate depending on the type of the BMP inhibitor to be used. For example, when any of proteinaceous inhibitors such as chordin, noggin and follistatin is used as a BMP inhibitor, the concentration of this inhibitor is in the range of 0.1 ng/mL to 1000 ng/mL, preferably 1 ng/mL to 500 ng/mL, more preferably 10 ng/mL to 100 ng/mL. When any of dorsomorphin, LDN193189 and DMH1 is used as a BMP inhibitor, the concentration of this inhibitor is in the range of 0.01 μM to 100 μM, preferably 0.1 μM to 10 μM, more preferably 0.5 μM to 1 μM.

In one embodiment, the combination of a TGFβ signal stimulator and a BMP inhibitor to be used at step (i-3) is a combination of TGFβ1 and DMH1.

At the cell culture step of (i-3), the basal medium may be further supplemented with any, or any combination, of fibroblast growth factor (FGF) 9, FGF20, BMP7, a retinoic acid derivative, and a GSK-3β inhibitor.

There is no upper limit on the number of days of cell culture at step (i-3), since no particular influence is exerted by long-term cell culture on the efficiency of RPC population production. For example, the number of days of cell culture is not less than 2 days, not less than 4 days, not less than 6 days, not less than 8 days, not less than 10 days, not less than 11 days, not less than 12 days, not less than 13 days, not less than 14 days, not less than 15 days, not less than 16 days, not less than 17 days, not less than 18 days, not less than 19 days, or not less than 20 days.

The cell culture at step (i-3) is performed at a culture temperature of, but not limited to, about 30 to 40° C., preferably about 37° C., and in an atmosphere of $CO_2$-containing air. The $CO_2$ concentration is in the range of about 2 to 5%, preferably about 5%.

2. Step (ii) of Sorting a Cell Population from the Cells Obtained at Step (i), by Using at Least One Cell Surface Marker Selected from the Group Consisting of CD9(−), CD55(−), CD106(+), CD140a(+), CD140b(+), CD165(+), CD271(+) and CD326(−), as well as the Sorting Method of the Present Invention:

At step (ii) and in the sorting method of the present invention (hereinafter in this section referred to collectively as "step (ii)"), a more highly purified cell population is sorted from the cells obtained at step (i), by using as an indicator the presence or absence of at least one cell surface marker selected from the group consisting of CD9, CD55, CD106, CD140a, CD140b, CD165, CD271 and CD326. More specifically, cell sorting is performed using an indicator requiring that cells be positive for CD106, CD140a, CD140b, CD165 and CD271, and negative for CD9, CD55 and CD326. In the present specification, the plus (+) symbol used for certain cell surface markers means that cells are positive for the certain antigens, and CD106(+), CD140a(+), CD140b(+), CD165(+) and CD271(+) are referred to as "positive selection markers". In this specification, the minus (−) symbol used for certain cell markers means that cells are negative for the certain antigens, and CD9(−), CD55(−) and CD326(−) are referred to as "negative selection markers". Also, the positive and negative selection markers may be referred to collectively as "cell surface markers".

In a preferred mode, the combination of cell surface markers to be used at step (ii) can be a combination of at least two, three or four cell surface markers selected from the group consisting of CD9, CD55, CD106, CD140a, CD140b, CD165, CD271 and CD326. For example, the combination of at least two cell surface markers preferably comprises a combination of one negative selection marker selected from the group consisting of CD9(−), CD55(−) and CD326(−) (preferably CD9(−)) and one positive selection marker selected from the group consisting of CD106(+), CD140a(+), CD140b(+), CD165(+) and CD271(+) (preferably the group consisting of CD140a(+), CD140b(+) and CD271(+)). The combination of at least three cell surface markers preferably comprises: a combination of one negative selection marker selected from the group consisting of CD9(−), CD55(−) and CD326(−) (preferably CD9(−)) and two positive selection markers selected from the group consisting of CD106(+), CD140a(+), CD140b(+), CD165(+) and CD271(+) (preferably the group consisting of CD140a (+), CD140b(+) and CD271(+)); or a combination of three positive selection markers selected from the group consisting of CD106(+), CD140a(+), CD140b(+), CD165(+) and CD271(+). The combination of at least four cell surface markers preferably comprises a combination of one negative selection marker selected from the group consisting of CD9(−), CD55(−) and CD326(−) (preferably CD9(−)) and three positive selection markers selected from the group consisting of CD106(+), CD140a(+), CD140b(+), CD165(+) and CD271(+). In one embodiment, the cell surface markers to be used at step (ii) are at least two or three cell surface markers selected from the group consisting of CD9(−), CD140a(+), CD140b(+) and CD271(+), preferably a combination of CD9(−), CD140a(+), CD140b(+) and CD271(+).

The cell surface markers for use at step (ii) can be used for sorting a cell population of RPCs derived from mammals including, but not limited to, humans. In the case of sorting a cell population of human RPCs, the NCBI accession numbers of the eight different human cell surface markers are as follows.

CD9: NM_001769.3 (SEQ ID NO: 1)

CD55: NM_000574.4 (SEQ ID NO: 3)

CD106: NM_001078.3 (SEQ ID NO: 5)

CD140a: NM_006206.4 (SEQ ID NO: 7)

CD140b: NM_002609.3 (SEQ ID NO: 9)

CD165: geneID_23449

CD271: NM_002507.3 (SEQ ID NO: 11)

CD326: NM_002354.2 (SEQ ID NO: 13)

The different human cell surface markers include genes having the nucleotide sequences of the corresponding accession numbers mentioned above, proteins encoded by said genes, and naturally occurring variants thereof.

Human CD9 is encoded by the gene having the nucleotide sequence of SEQ ID NO:1 (nucleotides 185 to 871), and has the amino acid sequence of SEQ ID NO:2. Human CD55 is encoded by the gene having the nucleotide sequence of SEQ ID NO:3 (nucleotides 295 to 1440), and has the amino acid sequence of SEQ ID NO:4. Human CD106 is encoded by the gene having the nucleotide sequence of SEQ ID NO:5 (nucleotides 222 to 2441), and has the amino acid sequence of SEQ ID NO:6. Human CD140a is encoded by the gene having the nucleotide sequence of SEQ ID NO:7 (nucleotides 332 to 3601), and has the amino acid sequence of SEQ ID NO:8. Human CD140b is encoded by the gene having the nucleotide sequence of SEQ ID NO:9 (nucleotides 470 to 3790), and has the amino acid sequence of SEQ ID NO:10. Human CD271 is encoded by the gene having the nucleotide sequence of SEQ ID NO:11 (nucleotides 126 to 1409), and has the amino acid sequence of SEQ ID NO:12. Human CD326 is encoded by the gene having the nucleotide sequence of SEQ ID NO:13 (nucleotides 359 to 1303), and has the amino acid sequence of SEQ ID NO:14. Human CD165 is a 37-42 kDa membrane surface protein, also known as AD2 or gp37. As an antibody specifically binding to CD165, the monoclonal antibody SN2 has been identified (Seon, B. K., et al., *J. Immunol.*, (1984), 132:2089-2095), and is now commercially available.

The naturally occurring variants of the aforementioned cell surface markers, in particular, CD9, CD55, CD106, CD140a, CD140b, CD271 and CD326, refer to cell surface markers encoded by genes whose nucleotide sequences have an identity of at least 80%, preferably at least 85%, at least 90%, at least 95%, or at least 98%, to the aforementioned nucleotide sequences, or cell surface markers comprising amino acid sequences having an identity of at least 80%, preferably at least 85%, at least 90%, at least 95%, or at least 98%, to the aforementioned amino acid sequences.

The "identity", as referred to herein with regard to nucleotide sequences or amino acid sequences, refers to an Identity value obtained by searching with the NEEDLE program (Needleman S. B., et al., *J. Mol. Biol.*, (1970), 48: 443-453) using the parameters available by default. The default parameters are as defined below.

Gap penalty=10
Extend penalty=0.5
Matrix=EBLOSUM62

Specific antibodies binding to the human cell surface antigens mentioned above are commercially available. Examples of such antibodies include those mentioned below in the Examples section. Cell surface markers maintaining the characteristic in that they are bound by commercial antibodies capable of specifically binding to each of the aforementioned cell surface markers are also included by the cell surface markers that can be used in sorting a cell population in the present invention.

The sorting of a cell population using a cell surface marker at step (ii) can be performed by any of various procedures known in the art. For example, cell sorting is performed using an antibody specifically binding to a cell surface marker, based on the binding of said antibody to the cells. Examples of such antibody-based sorting procedures include cell sorting with a cell sorter using a fluorescently labeled antibody (e.g., FACS® (BD Biosciences)), magnetic cell sorting using antibody-labeled magnetic beads (e.g., MACS® (Miltenyi Biotec)), and cell sorting using an antibody-immobilized carrier (e.g., cell enrichment column).

3. Therapeutic Agent for Renal Diseases, Renal Disease Treatment Method, and Method for Producing Cells for Renal Disease Treatment:

The RPC population acquired by the method of the present invention can be used as a therapeutic agent for renal diseases. Accordingly, this invention provides the following method for producing cells for renal disease treatment and the following method for sorting a cell population for renal disease treatment:

"A method for producing cells for renal disease treatment, the method comprising the steps of:
(i) culturing pluripotent stem cells under conditions that induce differentiation into renal progenitor cells; and
(ii) sorting a cell population from the cells obtained at step (i), by using at least one cell surface marker selected from the group consisting of CD9(−), CD55(−), CD106(+), CD140a(+), CD140b(+), CD165(+), CD271(+) and CD326(−)."

"A method for sorting a cell population for renal disease treatment from a renal progenitor cell-containing cell population using at least one cell surface marker selected from the group consisting of CD9(−), CD55(−), CD106(+), CD140a(+), CD140b(+), CD165(+), CD271(+) and CD326(−)."

As referred to in the present invention, the cells for renal disease treatment are cells characterized by at least one cell surface marker selected from the group consisting of CD9(−), CD55(−), CD106(+), CD140a(+), CD140b(+), CD165(+), CD271(+) and CD326(−), preferably cells characterized by CD9(−), CD140a(+), CD140b(+) and CD271(+).

The present invention provides a therapeutic agent for renal diseases comprising a RPC population produced by the production method of this invention or a RPC population sorted by the sorting method of this invention, as well as a method for treating a renal disease, the method comprising the step of administering to a patient a RPC population produced by the production method of this invention or a RPC population sorted by the sorting method of this invention. Exemplary procedures for administering a RPC population or a therapeutic agent to a patient include: application of a cell sheet made from an acquired RPC population onto the kidney of a patient; transplantation of an acquired RPC population suspended in physiological saline, etc. into the kidney of a patient directly or through blood vessels; transplantation of RPC aggregates obtained by three-dimensional culture on a scaffold formed of matrigel, etc.; loading a RPC population into a dialysis column; and administration of microcapsules encapsulating a RPC population. Exemplary renal diseases include chronic renal diseases including conditions not reaching chronic renal failure.

In the present invention, the number of RPCs contained in a therapeutic agent for renal diseases can be controlled to be increased or decreased as appropriate depending on the severity of disease, the size of an affected site, and/or body size.

EXAMPLES

Hereunder, the present invention will be described more specifically by way of examples, but the scope of this invention is not limited to these examples.

Example 1

<Two-Dimensional Scatter Plotting of a RPC Population by Flow Cytometry of OSR1 and SIX2 and Other Different Cell Surface Markers>

The iPS cells used in this example were OSR1-GFP & SIX2-tdTomato reporter human iPS cell lines generated by the procedure disclosed in NPL 3, which are capable of expressing GFP in conjunction with endogenous OSR1 gene expression and expressing tdTomato in conjunction with endogenous SIX2 gene expression. The human iPSC cell lines were induced to differentiate into a RPC-containing cell population by following the procedure disclosed in NPL 4. As a result of searching for cell surface markers specifically expressed in RPCs using Human Cell Surface Marker Screening Panel (BD Biosciences, Cat. No. 560747), CD9 (−), CD55(−), CD106(+), CD140a(+), CD140b(+), CD165 (+), CD271(+) and CD326(−) were identified as cell surface markers that enable clear fractionation of the RPC-containing cell population of interest (FIG. 1).

Example 2

<CD9(−)CD140a(+)CD140b(+)CD271(+) Cell Population Contains at Least 70% RPCs>

In this example, it was studied whether the percentage of RPCs present in cells fractionated from a cell population differentiated from human iPSCs can be increased by using a combination of some of the cell surface markers identified in Example 1.

First, it was studied whether the percentage of RPCs present in a cell population differentiated from human iPSCs can be increased by using one negative selection marker and three positive selection markers. The cell surface markers selected were CD9, CD140a, CD140b and CD271, which provided clear images of a discrete cell population in the two-dimensional scatter plots drawn as a function of OSR1 and SIX2 in Example 1. As antibodies against these cell surface markers, APC-H7 Mouse Anti Human CD9 (BD Biosciences; Cat. No. 655409), Alexa Fluor® 647 Mouse Anti-Human CD140a (BD Biosciences; Cat. No. 562798), BV421 Mouse Anti-Human CD140b (BD Biosciences; Cat. No. 564124), and BV510 Mouse Anti-Human CD271 (BD Biosciences; Cat. No. 563451) were used. The antibodies were used at 20-fold dilution, and cells were reacted with the antibodies at room temperature for 15 minutes. After the reaction, the reaction mixture was washed twice with PBS supplemented with 2% FBS, and analyzed using FACSAria™ III (BD Biosciences). Based on the resulting two-dimensional scatter plots, the CD9(−)CD140a(+)CD140b(+) CD271(+) cell fraction was demarcated to thereby fractionate said cell population. The fractionated cell population was analyzed again using FACSAria™ II, and the results showed that OSR1(+)SIX2(+) cells were present at a concentration of more than 70% in the entire cell population (FIG. 2B). FIG. 2A shows a set of flow cytograms for hiPSCs-derived differentiated cell groups stained with CD9, CD140a, CD140b and CD271. FIG. 2B shows a set of two-dimensional scatter plots of the flow cytometric measurements of OSR1 and SIX2 expression in hiPSCs before differentiation induction, in hiPSC-derived differentiated cell groups, and in a cell population after P3+P4+P6 cell sorting, respectively in order from left to right panels.

Example 3

<Formation of Renal Tubule-Like Structures Positive for LTL (Proximal Renal Tubule Marker) from the Cell Population Sorted by CD9(−), CD140a(+), CD140b(+) and CD271(+)>

RPCs are characterized by not only their expression of RPC markers but also by their ability to maintain differentiation potential into renal tubular cells. Accordingly, for the purpose of confirming whether the CD9(−)CD140a(+)CD140b(+)CD271(+) cells obtained in Example 2 were RPCs, the obtained cells were tested in a system for inducing differentiation into renal tubule. Differentiation into renal tubular cells and formation of renal tubule-like structures were determined based on expression of the proximal renal tubule marker LTL and morphological characteristics.

According to the procedure disclosed in NPL 4, the RPC-containing cell population into which the hiPSC lines had been induced to differentiate were immunostained with APC-H7 Mouse Anti Human CD9, Alexa Fluor® 647 Mouse Anti-Human CD140a, BV421 Mouse Anti-Human CD140b, and BV510 Mouse Anti-Human CD271 to fractionate the CD9(−)CD140a(+)CD140b(+)CD271(+) cells on FACSAria™ III. The fractionated cells were seeded at $1.0 \times 10^5$ cells/well on 96-well low-cell-adhesion spindle-bottom plates (Sumitomo Bakelite; Cat. No. MS-9096M) containing a UBC-conditioned medium (see below) supplemented with 50 ng/mL BMP7 (R&D; Cat. No. 354-BP-010) and 10 µM Y-27632 (Wako; Cat. No. 253-00513), and were cultured for 24 hours at 37° C. in an atmosphere of 5% $CO_2$-containing air. Next, the cells were cultured for another 24 hours, with the culture medium being replaced with a UBC-conditioned medium supplemented with 50 ng/mL BMP7, 0.5 µM BIO (Calbiochem; Cat. No. 361552) and 10 µM Y-27632. Then, the cells were cocultured with Wnt4-expressing NIH3T3 fibroblasts according to the procedure disclosed in NPL 4. The Wnt4-expressing NIH3T3 fibroblasts were used after they had been seeded at $4.0 \times 10^5$ cells/well on 24-well plates and treated with mitomycin C. The coculture was performed using a UBC-conditioned medium. After 2 weeks of coculture, cell staining was done. During the cell staining process, LTL-Biotin Conjugate (Vector Laboratories; Cat. No. B-1325) was used for primary reaction; Streptavidin-Alexa Fluor® 546 Conjugate (Life Technologies; Cat. No. S-11225) was used for secondary reaction; and Hoechst 33342 (Life Technologies; Cat. No. H3570) was used for nuclear staining. LTL was used at 200-fold dilution, and the reaction with LTL was done at 4° C. overnight. Streptavidin-Alexa Fluor® 546 Conjugate was used at 200-fold dilution, and the reaction with this conjugate was done at room temperature for one hour. As a result, it was observed that LTL-positive luminal structures were formed from the CD9(−)CD140a(+)CD140b(+)CD271(+) cell population (FIG. 3B). FIG. 3A illustrates the differentiation procedure into proximal renal tubule, in which cell aggregates are formed and cocultured with Wnt4-expressing NIH3T3 fibroblasts according to the same procedure as disclosed in NPL 4. FIG. 3B shows the appearances of the aggregates of CD9(−)CD140a(+)CD140b(+)CD271(+) cells cocultured with Wnt4-expressing NIH3T3 fibroblasts.

<UBC-Conditioned Medium>

The ureteric bud cell (UBC)-conditioned medium was prepared by a modified version of the procedure disclosed in the literature (Barasch et al., Am. J. Physiol., (1997), 273, F757-767). UBCs (gifted from Dr. Barasch, Columbia University; Proc. Natl. Acad Sci. USA, (1997), 94, 6279-6284) were cultured in a minimum essential medium (MEM; Invitrogen) supplemented with 10% FBS. After reaching 80% confluence, the cells were washed with PBS, and the culture medium was replaced with a DMEM/F12 (1:1) mixed medium supplemented with GlutaMAX, 10% KSR, 0.1 mM NEAAs, 0.55 mM 2-mercaptoethanol and 500 U/mL penicillin/streptomycin. Then, the cells were cultured for 3 days to produce a culture supernatant. The culture supernatant was filtrated through a 0.22 µm filter before use.

Example 4

<Percentages of RPCs (OSR1(+)SIX2(+) Cells) in Cell Populations Sorted by Different Combinations of CD9(−) with Three Positive Selection Markers>

The percentages of OSR1(+)SIX2(+) cells in cell populations sorted by all (10) exhaustive combinations of CD9(−) with any three of the positive selection markers extracted in Example 1 were investigated using FACSAria™ Fusion (BD Biosciences). Also, with regard to the particular combination of CD9(−), CD140a(+), CD140b(+) and CD271(+), which had been confirmed in Example 3 to allow fractionation of a RPC-containing cell population, it was investigated whether CD55(−) and CD326(−) can serve as negative selection markers alternative to CD9(−).

The antibodies used were: APC-H7 Mouse Anti Human CD9 (BD Biosciences; Cat. No. 655409); Alexa Fluor® 647 Mouse Anti-Human CD140a (BD Biosciences; Cat. No. 562798); BV421 Mouse Anti-Human CD140a (BD Biosciences; Cat. No. 562799); BV421 Mouse Anti-Human CD140b (BD Biosciences; Cat. No. 564124); BV510 Mouse Anti-Human CD271 (BD Biosciences; Cat. No. 563451); APC Mouse Anti-Human CD106 (BD Biosciences; Cat. No. 551147); BV605 Mouse Anti-Human CD106 (BD Biosciences; Cat. No. 563307); CD165-Biotin, Human (Miltenyi Biotec; Cat. No. 130-098-536); CD165-APC, Human (Miltenyi Biotec; Cat. No. 130-098-542); Anti-Human CD55 Biotin (eBioscience; Cat. No. 13-0559); and BV605 Mouse Anti-Human CD326 (BD Biosciences; Cat. No. 563182). The antibodies were used at 20-fold dilution, and cells were reacted with the antibodies at room temperature for 15 minutes, washed with PBS three times, and then analyzed. In the case of using the biotinylated antibodies, secondary staining was performed with BV605 Streptavidin (BD Biosciences; Cat. No. 563260) at 500-fold dilution. During the secondary staining process, cells were reacted with the indicated antibodies at room temperature for 15 minutes, washed with PBS three times, and then analyzed. The hiPSC-derived differentiated cell populations were analyzed using FACSAria™ Fusion, and based on the resulting sets of two-dimensional scatter plots, cell fractions stained with 12 different combinations of antibodies were demarcated to thereby fractionate the respective fractions of cells. The fractionated cell populations were analyzed again using FACSAria™ Fusion, to thereby compute the percentages of OSR1(+)SIX2(+) cells, OSR1(+)SIX2(−) cells, OSR1(−)SIX2(+) cells, and OSR1(−)SIX2(−) cells present in the whole cell populations (FIG. 4). The results found that high percentages of OSR1(+)SIX2(+) cells were found in the whole cell populations fractionated with all the combinations of markers.

Example 5

<Investigation of Cell Surface Marker Combinations that Allow Fractionation of RPCs>

Cell populations were analyzed by FACSAria™ Fusion using the antibodies against any combinations of the cell surface markers CD9, CD140a, CD140b and CD271 as adopted in Example 4, to thereby compute the percentage of OSR1(+)SIX2(+) cells present in each of the cell populations fractionated with different combinations of the negative selection marker CD9(−) with any positive selection markers selected from CD140a(+), CD140b(+) and CD271

(+). Also, the percentage of cells demarcated by each of different cell surface marker combinations in an unsorted cell population was investigated, and on that basis, the percentage of the number of OSR1(+)SIX2(+) cells collected using each of desired surface marker combinations with respect to the number of unsorted cells was computed (FIG. 5). The results revealed that condensation of OSR1(+)SIX2(+) cells was possible with the use of any of the different cell surface marker combinations, and that the percentages of OSR1(+)SIX2(+) cells condensed with different combinations of two or three cell surface markers were comparable to the percentage of OSR1(+)SIX2(+) cells condensed with a combination of four cell surface markers.

Example 6

<Investigation of Cell Surface Marker Combinations that Allow Fractionation of RPCs>

With the view to confirming that a high-purity RPC population can be fractionated even from hiPSC lines carrying no reporter gene by the use of the cell surface markers discussed above, hiPSCs (201B7 strain, gifted from Kyoto University) were tested in a differentiation induction system. The hiPSCs (201B7) were kept in maintenance culture by a conventional procedure (Takahashi K, et al., (2007), *Cell.* 131:861-72), and induced to differentiate into a RPC-containing cell population by following the procedure disclosed in NPL 4. Then, according to the same procedure as in Example 3, CD9(−)CD140a(+)CD140b(+)CD271(+) cells were fractionated using FACSAria™ Fusion to form cell aggregates, and the cell aggregates were cocultured with Wnt4-expressing NIH3T3 fibroblasts, whereby it was confirmed whether a cell population maintaining differentiation potential into renal tubule was successfully fractionated. Differentiation into renal tubule was determined based on expression of the proximal renal tubule marker LTL and morphological characteristics. As a result, it was confirmed that LTL-positive luminal structures can be formed from the CD9(−)CD140a(+)CD140b(+)CD271(+) cell population. In other words, it was demonstrated that a high-purity RPC-containing cell population can be fractionated even from hiPSCs (201B7)-derived differentiated cells by the use of CD9, CD140a, CD140b and CD271 (FIG. 6C). FIG. 6A shows a set of histograms of the number of cells as a function of fluorescence intensity of each of OSR1 (GFP), SIX2 (tdTomato) and the different cell surface markers. FIG. 6B shows a set of two-dimensional scatter plots of the flow cytometric measurements of CD9, CD140a, CD140b or CD271 expression in an iPSC 201B7 line-derived differentiated cell population. FIG. 6C shows an image of cell aggregates formed by sorting P4+P2+P3 cell populations and cocultured with Wnt4-expressing NIH3T3 fibroblasts.

Example 7

<Investigation of Cell Surface Marker Combinations that Allow Fractionation of RPCs (2)>

According to the same procedure as in Example 6, RPC-containing cell populations into which hiPSCs (201B7) had been induced to differentiate were subjected to immunostaining of surface antigens using APC-H7 Mouse Anti Human CD9, Alexa Fluor® 647 Mouse Anti-Human CD140a, BV421 Mouse Anti-Human CD140b, and BV510 Mouse Anti-Human CD271, and then to cell sorting with FACSAria™ Fusion to fractionate CD9(−)CD140a(+)CD140b(+)CD271(+) cells. The fractionated cells were smeared on slide glasses using Smear Gell® (GenoStaff; Cat. No. SG-01) and immunostained for intranuclear transcription factors. Anti-SIX2, Rabbit Poly (Proteintech; Cat. No. 11562-1-AP) was used as a primary antibody; Donkey Anti-Rabbit IgG (H+L) Secondary Antibody Alexa Fluor® 488 Conjugate (Life Technologies; Cat. No. A21206) was used as a secondary antibody; and Hoechst 33342 (Life Technologies; Cat. No. H3570) was used for nuclear staining. As a result of observation with a microscope (KEYENCE; Cat. No. BZ-9000), it was observed that the CD9 (−)CD140a(+)CD140b(+)CD271(+) cell population contains a higher percentage of SIX2-positive cells, which is one of the characteristics of RPCs, as compared with an unsorted differentiated cell population (FIG. 7).

INDUSTRIAL APPLICABILITY

As detailed hereinabove, the present invention provides a method for acquiring and producing high-purity RPCs from a RPC population into which PSCs are induced to differentiate, using a cell surface marker. The RPCs acquired by the method of this invention can be used in regenerative medicine for renal diseases such as renal failure.

SEQUENCE LISTING FREE TEXT

SEQ ID NO:15: L803-mts/GSK-3β peptide inhibitor; the 1st amino acid, glycine, is attached to myristic acid via an amide bond at the N terminus; the 11th amino acid, serine, is phosphorylated; and the 12th amino acid, proline, is amidated at the C terminus.

The invention claimed is:

1. A method for producing renal progenitor cells, the method comprising:
   (i) culturing human induced pluripotent stem (iPS) cells or human embryonic stem (ES) cells under conditions that induce differentiation into renal progenitor cells, wherein culturing comprises:
      (a) contacting the human iPS cells or human ES cells with a culture medium comprising at least one of Activin A, a GSK-3β inhibitor, or a retinoic acid derivative,
      (b) contacting the cells obtained from (a) with a culture medium comprising at least one of BMP7, a GSK-3β inhibitor, or a retinoic acid derivative, and
      (c) contacting the cells obtained from (b) with a culture medium comprising a TGFβ signal stimulator and a BMP inhibitor; and
   (ii) sorting a cell population from the cells obtained from (i), by selecting for cell surface markers: CD9(−), CD140a(+), CD140b(+), and CD271(+).

2. The method according to claim 1, wherein step (ii) further comprises selecting for at least one from the group consisting of CD55(−), CD106(+), CD165(+), and CD326(−).

3. The method according to claim 1, wherein step (ii) further comprises selecting for at least two from the group consisting of CD55(−), CD106(+), CD165(+), and CD326(−).

4. The method according to claim 1, wherein step (ii) further comprises selecting for at least three from the group consisting of CD55(−), CD106(+), CD165(+), and CD326(−).

5. The method according to claim 1, wherein step (ii) further comprises selecting for CD55(−), CD106(+), CD165(+), and CD326(−).

* * * * *